US008083861B2

(12) United States Patent
Labib et al.

(10) Patent No.: US 8,083,861 B2
(45) Date of Patent: Dec. 27, 2011

(54) APPARATUS AND METHOD FOR CLEANING PIPELINES, TUBING AND MEMBRANES USING TWO-PHASE FLOW

(76) Inventors: Mohamed Emam Labib, Princeton, NJ (US); Chung-Yue Lai, Lawrenceville, NJ (US); Yacoob Tabani, Basking Ridge, NJ (US)

( * ) Notice: Subject to any disclaimer, the term of this patent is extended or adjusted under 35 U.S.C. 154(b) by 0 days.

(21) Appl. No.: 12/321,321

(22) Filed: Jan. 16, 2009

(65) Prior Publication Data
US 2009/0229632 A1 Sep. 17, 2009

Related U.S. Application Data

(63) Continuation of application No. 10/464,173, filed on Jun. 18, 2003, now abandoned.

(51) Int. Cl.
*B08B 9/027* (2006.01)
(52) U.S. Cl. .............. 134/22.1; 134/22.11; 134/22.12; 134/22.18; 134/26; 134/34; 134/36; 134/42
(58) Field of Classification Search .............. 134/22.1, 134/22.11, 22.12, 22.18, 26, 34, 36, 42
See application file for complete search history.

(56) References Cited

U.S. PATENT DOCUMENTS

| | | |
|---|---|---|
| 2,151,671 A | 3/1939 | Wright |
| 2,222,516 A | 11/1940 | Powell et al. |
| 3,119,399 A | 1/1964 | Bender |
| 3,162,427 A | 12/1964 | Knudson et al. |
| 3,467,314 A | 9/1969 | Grubb |
| 3,551,331 A | 12/1970 | Cescon |
| 3,625,231 A | 12/1971 | Littrell, Jr. |
| 3,811,408 A | 5/1974 | Thompson |
| 4,166,031 A | 8/1979 | Hardy |
| 4,169,123 A | 9/1979 | Moore et al. |
| 4,209,402 A | 6/1980 | Gentles |
| 4,219,333 A | 8/1980 | Harris |
| 4,311,618 A | 1/1982 | Schafer-Burkhard |
| 4,375,413 A | 3/1983 | Geel et al. |
| 4,380,477 A | 4/1983 | Saunders |

(Continued)

FOREIGN PATENT DOCUMENTS
DE 893595 10/1953

(Continued)

OTHER PUBLICATIONS

Azzopardi, B., "Drops in annular two-phase flow," *Int. J. Multiphase Flow*, vol. 23, Suppl., pp. 1-53 (1997).

(Continued)

*Primary Examiner* — Sharidan Carrillo
(74) *Attorney, Agent, or Firm* — Merchant & Gould, P.C.

(57) ABSTRACT

An apparatus and method for cleaning passageways and the like with a two-phase mixture of gas under pressure and an aqueous cleaning solution. The two-phase cleaning mixture is generated in a module and is passed out of the module at a predetermined rate that determines droplet size, velocity and droplet density at the pipeline surface to be cleaned. The droplets impact the walls of the passageway to be cleaned, thereby fragmenting, eroding and removing contaminants in said passageway. These are then flushed out of the passageway by the two-phase flow. The flow of cleaning solution can be steady or pulsed. The apparatus and process include a clean-in-place system that is useful in food, beverage, pharmaceutical and similar process industries.

10 Claims, 7 Drawing Sheets

U.S. PATENT DOCUMENTS

| | | | |
|---|---|---|---|
| 4,400,220 A | 8/1983 | Cole, Jr. | |
| 4,444,597 A | 4/1984 | Gortz et al. | |
| 4,477,438 A | 10/1984 | Willcockson et al. | |
| 4,517,081 A | 5/1985 | Amiot et al. | |
| 4,525,220 A | 6/1985 | Sasa et al. | |
| 4,622,140 A | 11/1986 | Lee et al. | |
| 4,695,385 A | 9/1987 | Boag | |
| 4,707,335 A | 11/1987 | Fentress et al. | |
| 4,710,233 A | 12/1987 | Hohmann et al. | |
| 4,744,951 A | 5/1988 | Cummings et al. | |
| 4,767,539 A | 8/1988 | Ford | |
| 4,781,764 A | 11/1988 | Leenaars | |
| 4,787,404 A | 11/1988 | Klosterman et al. | |
| 4,863,688 A | 9/1989 | Schmidt et al. | |
| 4,881,563 A | 11/1989 | Christian | |
| 4,902,352 A | 2/1990 | Christian | |
| 5,007,461 A | 4/1991 | Naf | |
| 5,045,352 A | 9/1991 | Mueller | |
| 5,077,008 A | 12/1991 | Kralovic et al. | |
| 5,127,961 A | 7/1992 | Aiton | |
| 5,139,675 A | 8/1992 | Arnold et al. | |
| 5,160,548 A | 11/1992 | Boisture | |
| 5,178,830 A | 1/1993 | Riera Aixala | |
| 5,244,468 A | 9/1993 | Harris | |
| 5,279,799 A | 1/1994 | Moser | |
| 5,286,301 A | 2/1994 | Albrecht | |
| 5,322,571 A | 6/1994 | Plummer et al. | |
| 5,344,652 A | 9/1994 | Hall, II et al. | |
| 5,395,456 A | 3/1995 | Abrams et al. | |
| 5,408,991 A | 4/1995 | Iida et al. | |
| 5,415,191 A | 5/1995 | Mashino et al. | |
| 5,425,815 A | 6/1995 | Parker et al. | |
| 5,480,565 A | 1/1996 | Levin et al. | |
| 5,494,530 A | 2/1996 | Graf | |
| 5,529,701 A | 6/1996 | Grisham et al. | |
| 5,589,507 A | 12/1996 | Hall, II et al. | |
| 5,615,695 A | 4/1997 | Chambers | |
| 5,616,616 A | 4/1997 | Hall, II et al. | |
| 5,628,959 A | 5/1997 | Kross | |
| 5,635,195 A | 6/1997 | Hall, II et al. | |
| 5,651,893 A | 7/1997 | Kenley et al. | |
| 5,656,302 A | 8/1997 | Cosentino et al. | |
| 5,658,466 A | 8/1997 | Kawaguchi et al. | |
| 5,662,811 A | 9/1997 | Grisham et al. | |
| 5,698,100 A | 12/1997 | Levin et al. | |
| 5,714,060 A | 2/1998 | Kenley et al. | |
| 5,772,624 A | 6/1998 | Utterberg et al. | |
| 5,795,404 A | 8/1998 | Murphy et al. | |
| 5,840,343 A | 11/1998 | Hall, II et al. | |
| 5,855,216 A | 1/1999 | Robinson | |
| 5,896,828 A | 4/1999 | Kronschnabel et al. | |
| 5,915,395 A | 6/1999 | Smith | |
| 5,931,845 A | 8/1999 | Amyette | |
| 5,934,566 A | 8/1999 | Kanno et al. | |
| 5,941,257 A | 8/1999 | Gruszczynski | |
| 5,944,997 A | 8/1999 | Pedersen et al. | |
| 5,961,937 A | 10/1999 | Gobbato | |
| 5,972,875 A | 10/1999 | Crutcher et al. | |
| 6,027,572 A | 2/2000 | Labib et al. | |
| 6,050,278 A | 4/2000 | Arnal et al. | |
| 6,179,954 B1 | 1/2001 | Kawana et al. | |
| 6,192,900 B1 | 2/2001 | Arnal et al. | |
| 6,193,890 B1 | 2/2001 | Pedersen et al. | |
| 6,207,201 B1 | 3/2001 | Piacenza | |
| 6,261,457 B1 | 7/2001 | Wenthold et al. | |
| 6,326,340 B1 | 12/2001 | Labib et al. | |
| 6,423,152 B1 | 7/2002 | Landaas | |
| 6,447,990 B1 | 9/2002 | Alfa | |
| 6,454,871 B1 | 9/2002 | Labib et al. | |
| 6,619,302 B2 | 9/2003 | Labib et al. | |
| 6,717,019 B2 | 4/2004 | Lassila | |
| 6,773,395 B2 | 8/2004 | Takase | |
| 6,823,881 B1 | 11/2004 | Mishkin et al. | |
| 6,857,436 B2 | 2/2005 | Labib et al. | |
| 6,908,891 B2 | 6/2005 | Biering et al. | |
| 6,945,257 B2 | 9/2005 | Tabani et al. | |
| 7,762,949 B2 | 7/2010 | Nakao | |
| 2001/0047813 A1 | 12/2001 | Labib et al. | |
| 2002/0112743 A1 | 8/2002 | Tabani et al. | |
| 2002/0189647 A1 | 12/2002 | Labib et al. | |
| 2003/0062066 A1 | 4/2003 | Gruszcaynski et al. | |
| 2004/0007255 A1 | 1/2004 | Labib et al. | |
| 2004/0118413 A1 | 6/2004 | Williams et al. | |
| 2004/0118437 A1 | 6/2004 | Nguyen | |
| 2005/0028845 A1 | 2/2005 | Labib et al. | |
| 2005/0126599 A1 * | 6/2005 | Labib et al. | 134/22.11 |
| 2005/0150831 A1 | 7/2005 | Tabani et al. | |
| 2007/0027359 A1 | 2/2007 | Salman | |
| 2008/0264454 A1 * | 10/2008 | Tabani et al. | 134/22.18 |
| 2009/0229632 A1 * | 9/2009 | Labib et al. | 134/10 |
| 2010/0078046 A1 | 4/2010 | Labib et al. | |
| 2010/0078047 A1 | 4/2010 | Labib et al. | |

FOREIGN PATENT DOCUMENTS

| | | |
|---|---|---|
| EP | 160014 B1 | 11/1985 |
| EP | 213157 B1 | 3/1987 |
| EP | 490117 A1 | 6/1992 |
| EP | 289523 B1 | 1/1995 |
| EP | 634229 B1 | 1/1995 |
| JP | 49-102159 A | 9/1974 |
| JP | 49-116868 | 11/1974 |
| JP | 59-69019 A | 4/1984 |
| JP | 60-67896 A | 4/1985 |
| JP | 8019556 | 5/1994 |
| JP | 6121769 | 1/1996 |
| JP | 8-289687 A | 11/1996 |
| JP | 11104636 | 4/1999 |
| JP | 2002-66486 A | 3/2002 |
| RU | 1042826 A | 9/1983 |
| WO | WO 85/01449 | 4/1985 |
| WO | WO 86/05116 | 9/1986 |
| WO | WO 88/00494 | 1/1988 |
| WO | WO 95/10349 | 4/1995 |
| WO | WO 9620737 | 7/1996 |
| WO | WO 98/58632 | 12/1998 |
| WO | WO 99/29401 | 6/1999 |
| WO | WO 00/00306 | 1/2000 |
| WO | WO 01/91931 | 12/2001 |

OTHER PUBLICATIONS

Barajas, A. et al., "The effects of contact angle on two-phase flow in capillary tubes," *Int. Multiphase Flow*, vol. 19, No. 2, pp. 337-346 (1993).

Henstock, W. et al., "The Interfactial Drag and the Height of the Wall Layer in Annular Flows," *AIChE Journal*, vol. 22, No. 6, pp. 990-999 (Nov. 1976).

Hewitt, G. et al., "Annular Two-Phase Flow," *Pergamon Press*, pp. v-vii, 1-20, chapters 1-2 (Date Unknown).

Hobbe et al. "Use of Nuclepore Filters for Counting Bacteria by Fluorescence Microscopy," *Appl. and Environ. Microbiol.*, vol. 33, No. 5, pp. 1226-1228 (May 1977).

Klauer, J., "Piping: An examination of pipe self cleaning in high-purity water systems," *Ultrapure Water*, pp. 56-60 (Mar. 2001).

Kogure et al., "A tentative direct microscopic method for counting living marine bacteria," *Can. J. Microbiol.*, vol. 25, pp. 415-420 (1997).

Leypoldt, John K. & Cheung, Alfred K., "Characterization of Molecular Transport in Artificial Kidneys," Artifical Organs, International Society for Artifical Organs, vol. 20, No. 5, pp. 381-389, Jan. 1996.

Reinemann, D., "Dairy operators guide to milking machine cleaning and sanitation," *Paper written for presnetation at the NRAES the Milking Systems and Parlors Conference*, 8 pages (Jan. 30, 2001).

Riedewald, F., "Biofilms in Pharmaceutical Waters," *Pharmaceutical Engineering*, 8 pages (Nov./Dec. 1997).

Tragardh, C., "Cleaning in air-water-flow," *Division of Food Engineering, Lund Engineering, Alnarp (Sweden)*, pp. 424-429 (Date Unknown).

Triplett, K. et al., "Gas liquid two-phase flow in microchannels. Part 1: two-phase flow patterns," *International Journal of Multiphase Flow*, vol. 25, pp. 377-380, 387-393 (1999).

Woodmansee, D. et al., "Mechanism for the removal of droplets from a liquid surface by a parallel air flow," *Chemical Engineering Science*, vol. 24, pp. 299-307 (1969).

Web page print-out "510(k) Premarket Notification Database", 8 pages (Jan. 5, 2006).

Agreement between HDC Medical, Inc. and Guillermo J. Cohen Freue, 1 page.

Cameron, A., Basic Lubrication Theory, 3rd Edition, pp. 37-51, 93-125, John Wiley & Sons, New York, NY, (1981).

Fuller, D.D., Theory and Practice of Lubrication for Engineers, 2nd Edition, pp. 198-296, John Wiley & Sons, New York, NY, (1984).

Hays, "A Variational Approach to Lubrication Problems and the Solution of the Finite Journal Bearing," J. Basic Eng., 81:13-23 (1959).

Hubbe, "Detachment of Colloidal Hydrous Oxide Spheres From Flat Solids Exposed to Flow 1. " Experimental System, Colloids and Surfaces, 16:227-248 (1985).

Hubbe, "Detachment of Colloidal Hydrous Oxide Spheres From Flat Solids Exposed to Flow 2. " Mechanism of release, Colloids and Surfaces, 16:249-270 (1985).

Hubbe, "Detachment of Colloidal Hydrous Oxide Spheres From Flat Solids Exposed to Flow 3. " Forces of adhesion, Colloids and Surfaces, 25:311-324 (1987).

Hubbe, "Theory of Detachment of Colloidal Particles From Flat Surfaces Exposed to Flow," Colloids and Surfaces, 12:151-178 (1984).

Kabin, et al., "Removal of Solid Organic Films From Rotating Disks Using Emulsion Cleaners," J. of Colloid and Interface Sci., 228:344-358 (2000).

Leal, L.G., Laminar Flow and Convective Transport Processes: Scaling Principles and Asymptotic Analysis, pp. 396-406, Butterworth-Heinemann, Newton, MA, (1992).

Lee, et al., "Motion of a Sphere in the Presence of a Plane Interface. Part 1. An Approximate Solution by Generalization of the Method of Lorentz," J. Fluid Mech., 93:705-726 (1979).

Lee, et al., "Motion of a Sphere in the Presence of a Plane Interface. Part 2. An Exact Solution in Bipolar Co-Ordinates," J. Fluid Mech., 98:193-224 (1980).

Reynolds, "On the Theory of Lubrication and Its Application to Mr. Beauchamp Tower's Experiments, Including Experimental Determination of the Viscosity of Olive Oil," Philosophical Transactions of the Royal Society of London, England, 177:157-234 (1887).

Ryan, et al., "Colloid Mobilization and Transporting Ground Water," Colloids and Surfaces, 107:1-56 (1996).

Truskey, et al., "The Effect of Fluid Shear Stress Upon Cell Adhesion to Fibronectin-Treated Surfaces," J. Biomed. Mater. Res., 24:1333-1353 (1990).

Truskey, et al., "Relationship Between 3T3 Cell Spreading and the Strength of Adhesion on Glass and Silane Surfaces," Biomater, 14(4):243-254 (1993).

Yiantsios, et al., "Detachment of Spherical Microparticles Adhering on Flat Surfaces by Hydrodynamic Forces," J. of Colloid and Interface Sci., 176:74-85 (1995).

European Search Report for corresponding European Patent Application 03711147.3.

Alfa et al., "Worst-case soiling levels for patient-used flexible endoscopes before and after cleaning," AJIC (1999): 392-401.

Schrimm et al., "A new method for validating and verifying the cleaning of tubular instruments," Zentr Steril (1994) 2: 313-324.

Alfa et al., "Automated washing with the reliance endoscope processing system and its equivalence to optimal manual cleaning," AJIC (2006) 34 (9): 561-570.

Ross et al., "Standard test method for foaming properties of surface-active agents: Method D1173-53," Am Soc for Testing Materials, Philadelphia PA 1953: 1-2.

Landau et al., "Fluid Mechanics," Course of Theoretical Physics (1958): Pergamon Press.

Nakagawa et al., "Rivulet meanders on a smooth hydrophobic surface," Int. J. Multiphase Flow (1992) 18 (3): 455-463.

Nakagawa et al., "Stream meanders on a smooth hydrophobic surface," J. Fluid. Mech. (1984) 149: 89-99.

Ghezzehei, T., "Constraints on flow regimes in wide-aperture fractures," Lawrence Berkeley National Laboratory Paper LBNL 54681, 2004.

Le Grand-Piteira et al., "Meandering rivulets on a plane: a simple balance between inertia and capillarity," Laboratoire de Physique et Mecaniqu des Milieux Heterrogenes (2008): 1-5.

Schmuki et al., "On the stability of rivulet flow," J. Fluid. Mech. (1990) 210: 125-143.

Taylor G.I., "Non-interacting colloidal particles in an external field," Colloidal Hydrodynamics (1934) 146: 189-186.

Gomez-Suarez et al., "Analysis of bacterial detachment from substratum surfaces by the passage of air-liquid interfaces," Applied and Enviro. Mircobiology (2001) 67 (6): 2531-2537.

Gilles de Gennes, P., Capillarity and wetting phenomena, Springer (2003).

Office Action for Japanese Patent Application No. 2006-517312, dated Sep. 24, 2009.

Office Action for European Patent Application No. 04755377.1, dated Nov. 24, 2009.

* cited by examiner

APPARATUS AND METHOD FOR CLEANING PIPELINES, TUBING AND MEMBRANES USING TWO-PHASE FLOW

This is a continuation of U.S. application Ser. No. 10/464,173 that was filed with the United States Patent and Trademark Office on Jun. 18, 2003. The entire disclosure of U.S. Ser. No. 10/464,173 is incorporated herein by reference.

This invention relates to apparatus and method for removing contaminants adhered to a lumen surface. More particularly this invention relates to apparatus and method for cleaning passageways, pipelines, tubing and membranes of adherent contaminants.

BACKGROUND OF THE INVENTION

In order to achieve effective cleaning and removal of adhered substances or contaminants, including biofilm, proteins, carbohydrates, lipids, milk residues, deposits of food, beverages, contaminants of pharmaceuticals, including biopharmaceuticals and the like from equipment, piping and membrane surfaces, the adhesion forces between such contaminants and the surface to be cleaned must be overcome by the action of the cleaning process. To achieve good cleaning of such adhered residue or contaminants, the shear stresses generated by the cleaning process must be higher than the adhesive strength of the adhered contaminants to the surface to be cleaned. The simplest form of adhesion is due to van der Waals forces of attraction between the contaminant and the surface.

However, during actual industrial processing, other surface forces, such as electrostatic forces of attraction, acid-base interactions, hydrophobic forces, entanglement of contaminant molecules with roughness features of the substrate, or combinations of the above, are usually present between the surface of equipment or pipes and the contaminants to be removed. In these cases, the adhesion forces can become too high to be overcome with a simple circulation or flushing of cleaning liquids in the passageways, and thus cleaning cannot be achieved with such conventional means. When the contaminant is insoluble in the liquid employed in the cleaning operation, detachment of the contaminant from the surface and its subsequent flushing out from the pipeline, tubing and/or passageway are necessary to achieve good cleaning.

The physical nature of contaminants at a surface determines the extent and level of cleaning difficulty. The contaminant may be present on the surface as discrete particles or as layers of particles, in separate domains or areas covered by the contaminant. In the most difficult case, a continuous layer, as in the case of biofilm, food and dairy residues is present. Many cases of interest to the present invention relate to contaminants that are not soluble in the liquid or solution used in the cleaning process. The present invention is directed to cases when contaminants are mostly insoluble in the liquid used for a cleaning operation, when overcoming adhesion plays a considerable role in the cleaning process.

The conventional way to clean a pipeline, tubing or a passageway is to pass or circulate a liquid through the passageway. When the contaminant is present as discrete particles, or separate domains adhering to the surface, particle detachment, or contaminant domain detachment, by fluid (gas or liquid) flow must be achieved in order to clean the surface of the passageway. To achieve contaminant detachment, mechanical forces or shear stresses must be able to reach the contaminated surface. The ability to bring sufficient shear stress to the contaminated surface is a difficult task because of the fundamental limitations arising from the presence of a liquid boundary layer at the surface. The effect of the boundary layer on the ability to detach contaminants and clean surfaces of pipelines, tubing and passageways will be further explained below.

If the contaminant is present as discrete particles, and when there are several layers in the contaminant domain, it is possible to remove individual particles from the topmost layer of the contaminant domain. The removed particles then can be entrained and removed from the pipeline or passageway. It is possible that a whole section of the layer can be removed and entrained in a flowing fluid by a process called "denudation." However, the contaminant layer may be left behind at the surface if the forces generated by the flow condition are not sufficient to detach the entire contaminant, especially with the limitation imposed by the presence of a liquid boundary layer at the surface. This is the case with conventional liquid circulation cleaning methods. Further, if the flow conditions are not sufficient to carry the detached contaminant out of the pipeline or passageway, the detached contaminants can deposit back onto the surface, and re-attach to the surface, or become entrapped in the boundary layer of the liquid near the surface. Therefore, it is necessary in order to achieve cleaning to provide flow conditions to transport the detached contaminants outside of the pipeline, tubing or passageway.

The conventional way to decrease the adhesive strength of a contaminant adhering to a surface is to use surfactants in the cleaning solution. Surfactant molecule may transport to the gap between the particle and the surface, and adsorb in the gap. The adsorption of surfactants increases the separation distance between the particle and the surface to be cleaned, and thus achieves a decrease in the adhesion strength of the particle to the surface, and thereby enhances detachment and transfer of the solid into the flowing fluid. The degree of detachment from the surface depends on the contact area between the contaminant and the surface to be cleaned. In the case of discrete particles attached to the surface, the contact area is small and detachment is possible. As the contact area between contaminant and surface increases, the total adhesion force become too large for liquid flow to achieve contaminant detachment, even in the presence of surfactants and conventional liquid flow rates. The most difficult contaminant to remove is when the contaminant covers most or even the entire surface to be cleaned, as in the case of biofilm, or a completely coated surface of food residues or other contaminants that are numerous in industrial processing, including pharmaceutical and biopharmaceutical residues.

When the contaminant covers the entire surface of a passageway, such as in the case of biofilm, milk or protein residues, and when the thickness of the contaminant layer is large, it is difficult for the surfactant to reach the interface between the contaminants and the surface, and therefore the adhesive strength remains high for cleaning with conventional liquid circulation, even if the cleaning solution includes surfactants and other cleaning ingredients. Furthermore, in the case of liquid circulation at 5 feet/sec, as in the conventional clean-in-place (hereinafter C-I-P) cleaning method, the shear stresses created at the surface are too small to detach biofilm or protein layers. This is due to the presence of thick boundary layers and other complex limitations due to fluid dynamics, and due to the difficulty of transfer of shear forces to the surface to be cleaned. This normally leads to lengthy cleaning times and to the use of high pH fluids, such as caustic and other harsh chemicals.

The final result is always insufficient for good and efficient cleaning. The use of liquid flow also demands large amounts of cleaning liquids, rinse water and other liquids used in the process of CIP cleaning. The result of such limitation is both economic and environmental, including loss of production time, the cost of expensive chemicals, and consumption of large amounts of water for rinsing operations, in addition to the cost of neutralization and discharge of the waste generated from such cleaning operations. Cleaning processes may in some cases produce more waste to discharge than the production operation itself, a scenario common in food, pharmaceuticals, biopharmaceuticals and other industrial processes.

The contact area between biofilm and tubing, pipeline or passageway surfaces that carry water or other processing liquids, is very large, since it almost covers the entire lumen surface as compared to the small contact area of a discrete particle attached to the surface. Correspondingly, the adhesion force of biofilm, or other similar contaminants that cover most or the entire lumen surface of a passageway, becomes very large. In order to achieve detachment and removal of biofilm or similar substances, the contaminant needs to be fragmented to create cracks or holes in the continuous contaminant layer so that surfactant diffusion to the interface between the contaminant and the surface of a passageway becomes possible.

Fragmentation of biofilm and like contaminants is believed to be necessary to allow surfactant diffusion and adsorption at the interface between the biofilm and the surface. The latter process is important for decreasing the adhesive strength of the biofilm to the lumen surface (interior surface) of a passageway. Otherwise, the adhesive strength of biofilm to solid surfaces such as glass, metal or plastic, as measured by many investigators, ranges from 50 to 120 Pascals, which is too high for conventional liquid circulation to overcome, even in the presence of surfactants. Therefore, fragmentation and crack formation of biofilm and like contaminant layers is needed to allow the decrease of the adhesion forces between biofilm and a surface to a level that is amenable to cleaning and provides sufficient shear stresses created by the flow conditions used in cleaning operations. This fragmentation and crack formation is almost impossible to achieve with conventional liquid circulation which is too slow for many applications.

SUMMARY OF THE INVENTION

In accordance with the present invention, two phase flow of a gas and a liquid is generated and creates droplets of liquid that are formed and re-formed along the length of pipelines, tubing or passageways. The high velocities and controlled liquid to gas ratio of the flow, as well as the composition of the cleaning solution, provide conditions such that the liquid boundary layer is thin or non-existent. Droplets form and re-form continually, impacting the lumen surface to be cleaned. In the particularly difficult case of a highly adherent biofilm, droplet impact of the biofilm results in inertial hydrodynamic erosion of the biofilm layer that results in biofilm fragmentation and in the creation of cracks in the biofilm that allow surfactant molecules to diffuse and transport into the interface between the biofilm and the lumen surface of the pipeline, tubing or passageway. Using the two-phase flow of the present invention, the droplets that impact the surface are optimized with respect to size and velocity by the key flow parameters including; gas and liquid velocity, gas to liquid ratio, cleaning composition, surface tension equilibrium and dynamic surface tension properties of the cleaning solution, also taking into account the wetting properties of the lumen surface to be cleaned.

The droplets created by the two phase flow of this invention achieve biofilm fragmentation and detachment, and the biofilm fragments that are detached from the surface bounce back into the gas:liquid flow along with the droplets and become incorporated into the moving two-phase flow as it travels along the pipeline, tubing or passageway. Biofilm fragments can then be entrained in the air stream, or with the liquid fraction of the two-phase flow. Thus the detached biofilm is swept along and flushed out of the passageway during this cleaning process.

The embodiments of the invention include apparatus and process for cleaning, rinsing and sanitizing/disinfecting tubing, pipelines, passageways including hollow membranes and other equipment. The combination of the apparatus and cleaning process according to the invention further includes a clean-in-place (hereinafter C-I-P) systems for use in food, beverage, pharmaceutical and other industries.

DETAILED DESCRIPTION OF THE INVENTION

Figure 1:
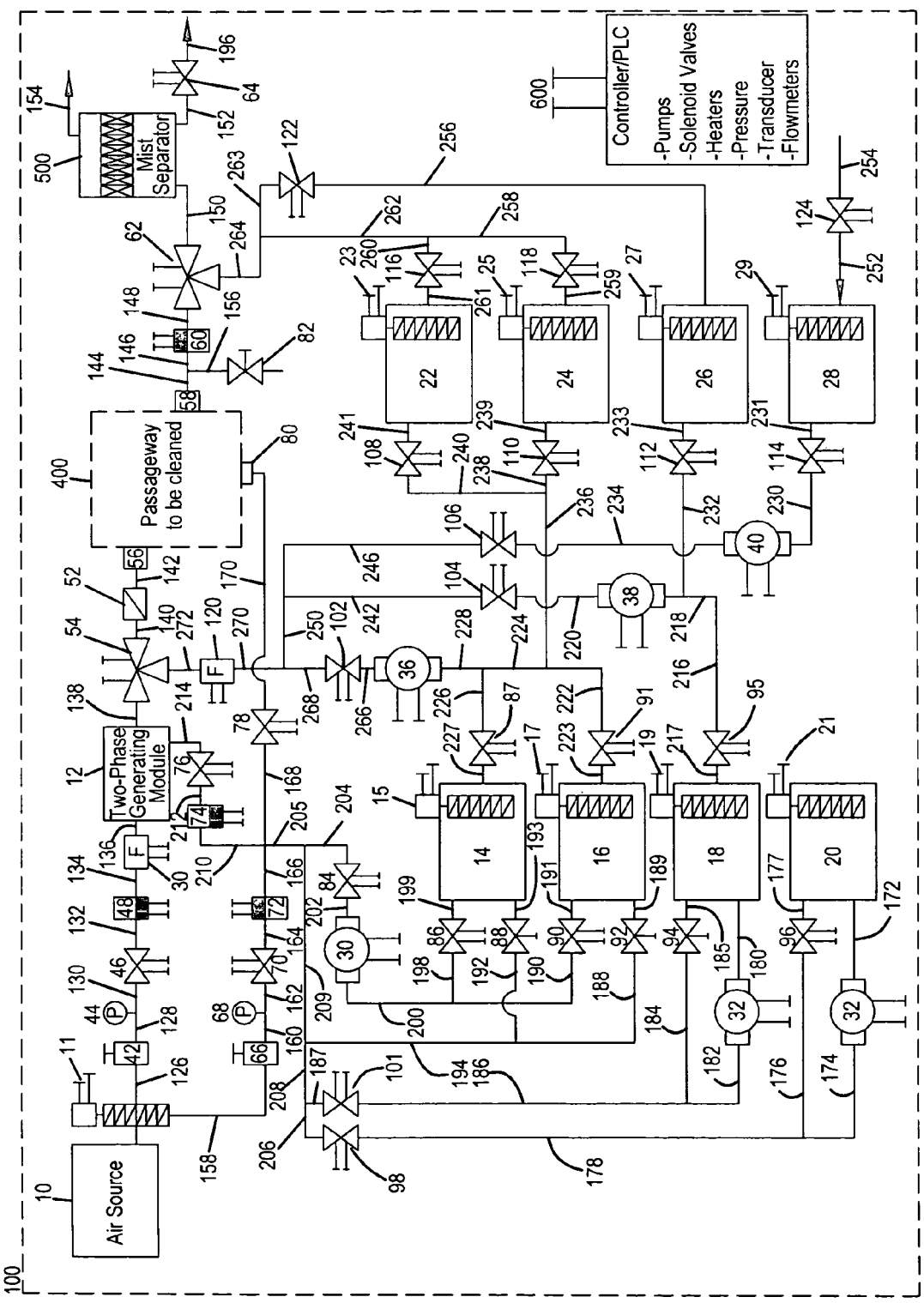
FIG. 1 is a schematic view of an apparatus for carrying out the present cleaning method.

The term "passageway", as used herein, includes, inter alia, pipelines, tubing and hollow membranes.

According to the two-phase flow cleaning method of the present invention, droplet size plays an important role in the cleaning process since the inertial impact of the droplet is tangible, and become very significant at the optimal droplet size, between 30 to 200 microns. Droplets that are too small have inertial impact forces that are too low to achieve fragmentation and detachment of biofilm and like contaminants from the lumen of passageways. The larger the droplet, the larger is its kinetic energy, and the larger is biofilm fragmentation for example. However, in the two-phase flow of this invention, the optimal droplet size is determined by the flow conditions and parameters mentioned above. The two-phase flow of the present invention optimizes droplet size without compromising the main flow attributes needed to cover the entire lumen surface and length of the passageway to be cleaned; and at the same time ensure that the liquid boundary layer is either very thin or discontinuous. The purpose of the latter condition is to keep the contaminant bare such that the droplets directly or nearly directly impact the contaminants, causing their fragmentation, erosion and detachment. Droplets that are too small are not effective for cleaning and thus can be entrained in the gas phase without impacting the lumen surface of the passageway. On the other hand, very large droplets, e.g., those that are >200 microns in size are difficult to create and re-suspend (in the gas flow) in an efficient manner.

In accordance with the present invention, the best droplet sizes are in the range between 30 and 200 microns, and preferably they are about 50-150 microns. Again, as the droplets leave the surface, biofilm fragments become attached to them, and as this process continues, more and more of the biofilm is eroded from the lumen surface of the passageway. As holes and cracks in the film are created by this process, surfactant molecules and small ions diffuse to the interface and lower the adhesion of the biofilm to the surface. As a result, as the cleaning proceeds, the remaining biofilm becomes easier to detach and remove by the fast moving two-phase flow.

Complete coverage of the lumen surface of a passageway with droplets along the entire surface area and length ensures the complete removal of biofilm and like contaminants from various passageways having varying diameters. According to the present invention, passageway diameters from 150 microns to more that 12 cm can be cleaned with the present two-phase flow system, including cleaning of diverse contaminants ranging from biofilm to protein layers to dairy and food residues, spores, blood residues and the like.

According to this invention, the conditions needed to remove biofilm and other adherent substances, such as dairy or milk residues, blood clots, protein layers, and foulants such as those encountered in membranes used in waste water treatment, with the two-phase flow system from the lumen of passageways include: an initial droplet formation device at the beginning of the passageway that creates droplets of between about 25 to 200 microns but up to 400 microns. This is done by adjusting the liquid to gas ratio, gas and liquid flow rates, solution chemistry and droplet break-up properties of the cleaning solution so that a sustained droplet formation and re-formation takes place along the entire length and lumen surface area of the passageway. Under proper conditions, passageways having a large length:diameter (hereinafter L/D), such as a diameter of from about 1 mm to about 10 cm, and a length up to 100-300 meters can be cleaned in accordance with the invention.

In addition, and simultaneously, a condition of complete coverage of the surface with droplet impact needs to be achieved, along with creation of droplets of more or less uniform size, so as to create a sufficient localized shear and other mechanical stresses when they impact the surface of the passageway. Therefore, droplet impact should be made sufficient for the destruction of any section of biofilm remaining at the surface. Further, the process must be applied for a sufficient time sp that complete removal of the biofilm fragments, or like contaminants, is completed from the entire lumen surface of the passageway being cleaned. Again, in order to ensure that the inlet of the passageway, especially one with a large L/D, is cleaned, the droplets must be injected into the passageway with the aid of a nozzle into the air stream near the entrance of the passageway. In addition, the average droplet size must remain in the range between 30 to 200 microns, preferably between about 50-150 microns, because large droplets will have small penetration depth, and thus can experience problems due to gravity and other effects.

Further, according to the present invention, the flow condition must be made to cover the entire circumference of the lumen of the passageway so that the lumen surface receives uniform coverage and uniform droplet impact during the cleaning. This condition must be satisfied for horizontal, vertical and positions in between, since piping systems in industrial processes have various orientations and arrangements. To achieve this condition, the two-phase flow velocity, and the liquid fraction of the two-phase flow mixture must be adjusted to create these coverage conditions. Therefore, a minimum gas velocity must be used and the gas velocity and the liquid to gas ratio must be adjusted for different diameter passageways and surface wetting conditions of the lumen surface to be cleaned. Further, according to this invention, the surface of the contaminant must be bare, or almost bare, of a liquid layer so that droplet impact achieves the most effective fragmentation of the contaminant layer and thus effects cleaning of the lumen of the passageway.

We believe that the most favorable condition for cleaning is a special form of the annular mist regime in two-phase flow or other regimes in its vicinity that satisfy droplet formation and instability of the boundary layer, one where droplet formation, droplet deposition and droplet impact at the lumen surface is maximized for the purpose of cleaning, but where the liquid boundary layer thickness is minimal, and preferably where the surface of the passageway is not entirely covered by a thick liquid film. The condition favorable for cleaning according to the present invention is distinct from the well-known annular film flow, where the lumen of the passageway is covered with a continuous liquid film, and where droplet formation is kept to minimum. The latter flow regime is not efficient for cleaning since the droplet formation and impact is inadequate. In the present invention, extensive droplet formation and droplet impact are required for fragmentation of biofilm and like contaminants. Droplet impact creates a localized shear. This localized shear has been estimated to be 100 to 1000 times more than the bulk shear generated during liquid circulation at about 5 feet/sec, as is present in conventional C-I-P systems.

In the stratified flow regime, only the bottom of the tubing or passageway is in contact with the liquid, while the top portion of the lumen is bare of cleaning liquid. Therefore, the cleaning in this case is worse than cleaning with liquid circulation only. Also, other two-phase flow regimes, including bubble flow, slug flow and others that completely cover the lumen surface, are not very different from a liquid circulating regime. The main function of air in the above flow regimes, where the liquid is the major phase, is to increase the velocity of the liquid in the passageway; however, the shear stress generated is still defined by the bulk shear due to liquid flow. Thus the magnitude of the shear stress is too low to remove highly adherent contaminants such as biofilm and the like, and the liquid boundary layer remains thick enough to hamper removal of surface contaminants. The two-phase flow of the present invention is thus different in mechanism and in the magnitude of shear stresses generated due to droplet impact. Further, there are additional surface forces that assist in cleaning during two-phase flow according to this invention due to pulling of droplets from liquid domains formed from droplet coalescence during the formation and re-formation of droplets along the length of the passageway. As droplets are pulled away from the surface, they exert other types of forces (other than droplet impact) due to surface tension forces and other complex surface phenomena during the two-phase cleaning, and these forces are important in increasing cleaning efficiency.

We have shown that a two-phase flow regime that creates and sustains high velocity droplets can fragment and remove biofilm in several applications. In the optimal regime for cleaning we identified that droplet formation, droplet deposition and then droplet re-formation are necessary for cleaning. Droplet formation and re-formation as well as droplet deposition density at the lumen surface to be cleaned should be kept at a condition optimal for cleaning, while simultaneously ensuring that wetting and de-wetting dynamics at the surface are favorable for cleaning and preventing formation of a thick boundary layer. We found, using a clear or transparent tubing with the aid of a microscope, that the optimal cleaning condition occurs when gas velocity and the liquid:gas ratio are adjusted so that droplet formation becomes optimal, and when the droplet deposition rate is maximized. This ensures that the droplets impact the bare surface of biofilm, for example. When droplet deposition does not form a continuous liquid film on the lumen surface, fragmentation and cleaning can take place. Therefore, the correct regime is different from the annular flow regime, where liquid flow forms a film along the walls of the passageway and the gas flows near the center, as described in the prior art. In addition, we have found that the presence of surfactants and the wettability of the passageway surface significantly affect the physical form of the liquid that is created by droplet impact and deposition. Surfactants were found to aid the process of wetting and de-wetting at the lumen surface of the passageway in a way so as to achieve the condition of droplet formation, a thin boundary layer, bare areas of surface, and impact shear stresses in this cleaning process.

A critical sub-process during the cleaning of passageways with high L/D is the re-formation of droplets after they impact the lumen surface along the length of the passageway. As droplets impact the surface, droplets that land nearby each other coalesce to minimize their surface energy, and to form a liquid domain that is then, either fully or partially, ripped off by the gas flow to form new droplets. The flow conditions of the present invention do not allow the liquid to accumulate, or to form a continuous thick film on the lumen surface, but rather to facilitate the dispersion of the coalesced droplets very quickly and re-form other droplets that are then carried by the flow.

Droplet breakup at the interface during two-phase flow cleaning may take place by one or more modes, depending on the cleaning solution surface chemistry, static and dynamic surface tension and wetting, viscosity and flow conditions, particle gas velocity and liquid-to-gas ratio; also the wetting properties of the surface to be cleaned plays an important part in this process. The known modes of liquid breakup include either "bag breakup" or "ligament breakup", or a combination of the two, and even more complex forms.

In the case of "bag breakup" the gas may flatten a body of a liquid, created by coalesced droplets at the surface, to form a bag-shaped body of liquid with thin walls. These then burst as the liquid wall becomes very thin, to form new droplets that travel with the flow, and can impact another location downstream at the surface and thus achieve cleaning.

In the case of "ligament breakup", the same sequence of breakup is achieved but the body of the liquid domain is in the form of a ligament which then breaks up into individual droplets that become a part of the flowing two-phase flow, i.e., they travel downstream, impact the surface at another location, and the process is repeated until the liquid exits the passageway. It is possible to have a combination of the two modes or mechanism of droplet re-formation taking place during the cleaning process with the two-phase flow, depending on the conditions of surface chemistry, of surface and cleaning solutions, dynamic and static surface tension, dynamics of the wetting and de-wetting processes, liquid viscosity, the flow conditions and the like.

Irrespective of the exact detailed mechanism of droplet re-formation, the two-phase flow of the present invention should sustain the formation and re-formation of droplets over the entire length of the passageway, even in the case of a very long pipeline (>300 feet in some cases). Fortunately, since the velocity of the gas increases as the gas expands as it travels downstream to the open end of the passageway due to a pressure drop (passageway volume is constant), the formation and re-formation of droplets and their velocity increases towards the open end of the passageway. This feature is important with respect to being able to sustain an active two-phase flow optimal for the cleaning of the lumen of long passageways with a high L/D. In fact, we discovered that the cleaning towards the outlet end of pipelines is usually easier to accomplish compared to the front end, due to the increase in droplet velocity as the flow travels to the open end for the reasons described above.

Furthermore, we have also found that the cleaning efficiency at the front end of the passageway must have optimal two-phase flow conditions with sufficient droplet impact and droplet formation and re-formation (velocity, liquid to gas ratio, liquid surface tension, etc.) to ensure that the front end of the passageway is properly cleaned. According to the present invention, we found that if the flow is adjusted for cleaning of the front section of a long passageway (where the two-phase flow is injected), the other open end of the passageway will always receive higher velocity droplets and thus the cleaning of the entire passageway can be achieved.

The velocity change between the inlet and outlet of passageways during two-phase flow cleaning is provided in the examples below. It is important to adjust the liquid:gas ratio at the entrance of a passageway so that, when the gas expands downstream, an optimal liquid:gas ratio still remains in the optimal range for cleaning, i.e., is sufficient to generate enough droplet deposition density within the size range needed to clean the section near the outlet of the passageway.

Yet another important feature of the invention is the size of the droplets that are formed in the two-phase flow, and consideration of the change in gas velocity as the two-phase flow travels from the entrance to the outlet of the passageway. If the droplets become too small towards the end of the passageway, a larger fraction becomes entrapped in the gas and thus not enough droplet impact density is achieved, resulting in a less than optimal cleaning towards the outlet end of the passageway. In such case, it is possible to overcome the above limitation by adjusting the gas:liquid ratio at the entrance of the passageway, or at a location along the length of the passageway, so that the optimal gas:liquid ratio needed for cleaning is achieved for the entire length of the passageway. It is clear that these conditions can be varied to clean different passageway types for different applications by using the ranges and conditions as exemplified below.

Further, in order to achieve cleaning according to this invention, the two-phase flow must produce uniform droplet deposition along the entire surface of the passageway as the flow travels from inlet to outlet, and the droplet impact on the surface of the contaminant must create sufficient shear and other mechanical stresses so as to destroy any section of the biofilm or the contaminant present on the surface of the passageway. The above conditions must be capable of achieving fragmentation of the biofilm or the contaminant layer, and ultimately achieve the detachment and removal of the entire layer from the lumen surface of the passageway. Droplet deposition density onto the lumen surface to be cleaned is an important variable that controls the efficiency of the cleaning process, and this is directly related to droplet size, flow conditions and the liquid fraction of the two-phase mixture. Droplet size is a function of the cross section (diameter), of the passageway, the liquid mass flux in $kg/m^2.sec$, the gas mass flux in kg/m².sec, the surface tension and, to some extent, the viscosity/rheology of the liquid. Therefore a superficial gas velocity in excess of 10 meters/sec covers the effective range of cleaning, and is preferably between 20 and 100 meters/sec near the inlet of the passageway to be cleaned; the velocity of the gas increases as it travels though the passageway towards the outlet end.

Furthermore, we have found that droplet dimensions differ with the cross section of the passageway, with the gas velocity and the liquid mass flux. The latter may have to be varied by experimentation in order to obtain effective droplet size, droplet velocity, droplet deposition density, and at the same time ensure that the surface of the pipeline is not flooded with a liquid layer, or forms a film that could mask or shield the biofilm or the contaminant present from direct or close direct impact by the droplets. By manipulating the above parameters, one can achieve the proper conditions for cleaning.

The condition at the lumen surface of the passageway during cleaning with the two-phase flow of this invention is very important to achieving effective cleaning. The wetting properties of the surface to be cleaned also play an important role in the cleaning process, especially with respect to the nature of the liquid that accumulates as droplets impact the surface and coalesce on the lumen surface during the two-phase flow cleaning. If the surface has a low contact angle (the surface is wettable), the liquid that accumulates as the result of droplet coalescence will tend to spread out to cover a larger area compared to a surface with a high contact angle with the cleaning liquid. Furthermore, this spreading is a complex process, especially because it is transient in nature, and at the same time is subjected to the dynamic conditions of the two-phase flow. These events last only tens of a millisecond and they cannot be readily explained with equilibrium wetting knowledge as is known in the field of surface chemistry. Visual observation shows that a complex process involving a very dynamic spreading process at the surface during the cleaning with the present methods. It is important to adjust the conditions to avoid forming thick or continuous liquid films at the surface during the cleaning with the two-phase process. These parameters in many cases require controlling the flow conditions and can be visually seen using a transparent section of the passageway.

Also, according to this invention, the presence of a surfactant in the cleaning liquid plays an important role with respect to droplet formation, droplet size and the nature of the liquid domains that accumulate on the surface during the two-phase cleaning. Specifically this is relevant with respect to issues related to the dynamic surface tension properties of the cleaning liquid. Equilibrium surface tension of a surfactant solution is the value of surface tension (dynes/cm) that is measured when surfactant molecules accumulate at the liquid/water interface and are in equilibrium with surfactant molecules in the bulk solution. This is usually measured by the conventional "ring method" or other techniques as known in the prior art; these methods usually require several minutes to obtain a measurement. Therefore, equilibrium surface tension is measured when the liquid/water interface is at equilibrium and it is independent of the diffusion rates of surfactant molecules from the bulk of the liquid to a newly created air/water interface. Most surfactant suppliers only specify static or equilibrium surface tension values in the information bulletins they provide to their users.

On the other hand, dynamic surface tension describes the surface tension behavior as a function of time, usually in time scale from zero to about 100-200 milliseconds, or longer. This is usually presented as a plot of dynamic surface tension (mN/m) versus surface age in milliseconds. For many surfactants, it takes sometimes seconds or minutes for the surface tension values to reach their equilibrium values. On the other hand, dynamic surface tension depends on the diffusion rates of surfactant molecules to reach the newly created interface, as is the case of dynamic processes such as the formation of new droplets or the spreading of liquid droplets after they impact the surface, such as the case during the two-phase flow process of the present invention. We found that the dynamic surface tension behavior of the cleaning solution is important for droplet break up, droplet formation, droplet re-formation, and physical spreading of the liquid on the surface to be cleaned. In the present invention, we found that pure water only, having a surface tension of 72 mN/m, is difficult to use in some applications due to the difficulty of forming droplets during the two-phase flow cleaning process, and it is possible to use water only except when the gas velocity used is very high. In the case of water alone, we observed that water tends to segregate into slug and such slugs move alone followed by periods with only gas flowing in the passageway; this mode of two-phase flow was found to be unfavorable for cleaning. However, when a surfactant is used in the cleaning solution, droplet formation and re-formation becomes possible, and the behavior of the liquid deposited at the surface to be cleaned tends to satisfy the conditions required for cleaning, i.e., the liquid domains become smaller, and re-disperse very readily.

We found that the use of proper surfactants ensures ready formation of the two-phase flow with droplets at reasonable velocities, and that the surface of the passageway to be cleaned is not covered with a continuous liquid film and where the contaminant surface remains more or less bare, so that impact of the liquid droplets effects fragmentation and removal of the biofilm or contaminant. It is thus important to select surfactants with certain properties of dynamic surface tension and dynamic wetting and de-wetting properties.

Examples of surfactants that do not foam in the two-phase cleaning liquid are set forth below in the Examples. It is also possible to add a de-foaming agent to solve a foaming problem, if necessary. However, it is important to consider several parameters to arrive at the proper choice of a successful surfactant for two0-phase cleaning, including: dynamic and static surface tension properties; the dynamics of wetting and de-wetting; foaming and foaming dynamics.

The selection of an optimal cleaning solution for two-phase cleaning also includes the pH, chelating capacity, and oxidation-=reduction properties. Therefore the present invention includes th4e use of those surfactants and composition, in combination with the two-phase fluid dynamic parameters and the nature of surface processes, as described in the present invention.

The following parameters illustrate conditions that were found to achieve 99.6% removal of bacterial cells and a biofilm matrix;
Inlet velocity, 104 feet/second
Two-phase cleaning time, 20 min.
Rinsing time, 10 min.
Air volume, 27.4 SCFM
Liquid-to-gas ratio: inlet, 1/4000 and outlet, 1/14000 Cleaning solution is alkaline with a pH of 11.5

Visual observation of the two phase flow that was found to be effective in removing biofilm revealed that optimal biofilm removal took place when the two phase flow mixture flowing in the passageway contained liquid droplets that continually impacted the lumen surface of the pipeline. Further, the optimal removal was achieved when part of the lumen surface was not covered by a liquid film, and when surface de-wetting was accomplished by adjusting the gas to liquid ratio and the gas velocities in the ranges indicated above. It is important to note that when we use passageways having different internal diameters. Adjustment of the gas:liquid ratio is required to achieve the two-phase flow condition that provides liquid droplets that impact the lumen surface and prevent the formation of a liquid film on the surface of the passageways.

Further, the two-phase flow apparatus and method are applicable for performing cleaning followed by rinsing and sanitizing steps. These steps can be used either together, or in any combination, as required for the purposes of various processes. The apparatus and method set forth herein, and their variations, should be considered as a means to deliver chemical cleaning agents, sanitizing agents and rinsing liquids to passageways, as employed in industrial processes.

During a sanitizing step using the two-phase flow process, the gas:liquid ratio may be the same or different from that used in cleaning or rinsing steps. The nature and behavior of the two-phase flow at the surface or a passageway that achieves effective sanitization was found to be somewhat different compared to the cleaning step. During a sanitizing step, the lumen surface using the two-phase flow process, droplet impact forces are not as critical as during the cleaning step, and the nature of the two-phase flow at the surface requires a different set of manipulations. The two-phase flow condition in this case needs to ensure that the entire surface of the passageway is covered with the sanitizing solution for a set period of time to accomplish disinfection. A slightly lower gas:liquid ratio would be expected to perform better sanitization.

An apparatus 100 suitable for carrying out the methods of the invention is shown in FIG. 1.

A passageway to be cleaned 400 is connected to a two-phase flow generating module 12 connected in turn to an air source 10 and a holding tank for cleaning solution 14. The passageway to be cleaned 400 is directly connected to an inlet adapter 56 and an outlet adapter 58.

A pipe 142 is used to inlet the air-fluid mixture through inlet adapter 56. A pipe 170 feeds a backflushing liquid into the passageway 400 via an inlet adapter 80. When backflushing is complete, the mixture exits through the outlet adapter 58 via the pipe 144.

The two-phase generating module 12 is used to combine the pressurized air from air source 10 and a pre-defined amount of liquid from the holding tank 14 to generate droplets that are carried along with the air stream and delivered to the passageway to be cleaned 400. The two-phase generating module 12 includes an air inlet pipe segment 136, and a liquid inlet pipe 214. The two-phase generating module 12 also includes a two-phase mixture outlet pipe 138. The two-phase generating module 12 mixes pressurized air and a pre-defined amount of liquid for generating droplets that are carried along with the air stream to perform cleaning, rinsing or sanitizing of the passageway to be cleaned 400. The two-phase generating module 12 includes an air inlet port 134 that is connected to pipe segment 136, and a liquid inlet port that is connected with pipe segment 214. A P-type fine atomization nozzle 13 such as those manufactured by Bete Fog Nozzle, Inc. is installed at the liquid inlet of the module 12 to generate liquid droplets in the range between 25 and 400 microns in diameter. Selection of the nozzle 13 and droplet range may depend on the nature of the passageway to be cleaned and other factors. The two-phase generating module 12 also includes a two-phase mixture outlet that is connected with pipe segment 138. A typical design of the two-phase generating module using a nozzle to break up the liquid in the form of droplets is shown in FIG. 2A.

Figure 2:
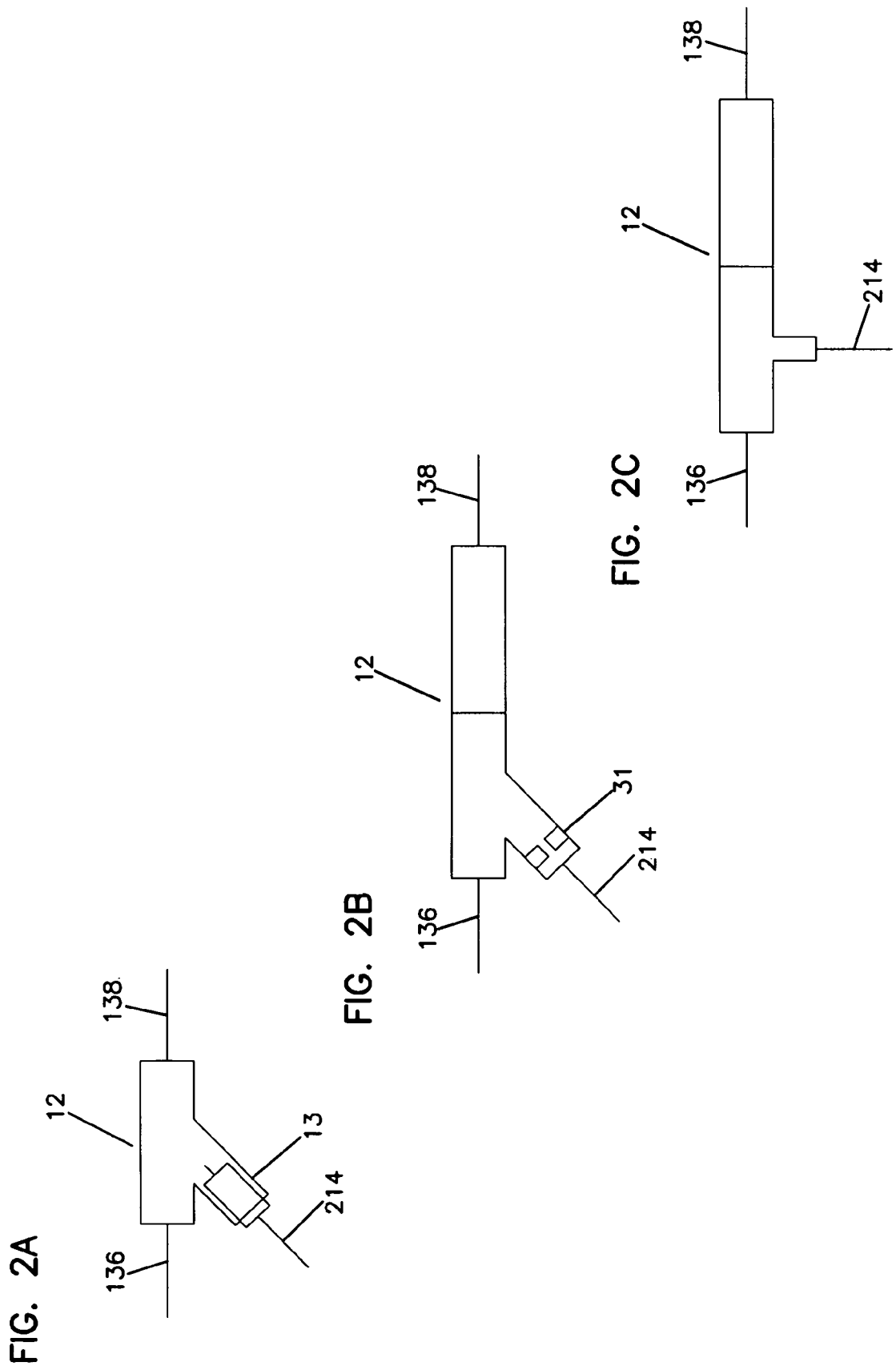
FIG. 2A illustrates a cross sectional view of a two-phase generating module with a nozzle used to form a two-phase flow including droplets.
FIG. 2B illustrates a cross sectional view of another embodiment used to create a two-phase flow including droplets.
FIG. 2C illustrates a cross sectional view of a two-phase generating module to create two-phase flow including droplets using a T-connection.

A second type of two-phase generating module is shown in FIG. 2B where the nozzle is replaced by an orifice 31. This type of design is used in some cases especially when the passageway to be cleaned is small or complex in shape, or when the passageway is narrow and it is possible to create the requisite two-phase flow with droplets without the aid of a nozzle at the entrance of the system to be cleaned. The main function of the orifice in this case is to provide a fixed amount of liquid to mix with air for generating a two-phase mixture with a known gas to liquid ratio. The two-phase generating module 12 using orifice 31 is usually equipped with a long section of tubing (expansion section), to allow the liquid-gas mixture enough time to form droplets in the air stream and to reach some sort of steady state before entering to the passageway to be cleaned 400.

Yet another version of the two-phase generating module 12 is shown in FIG. 2C where liquid is introduced into the air stream through a T-connection. Again, this type of design is usually accompanied with a long pipe or tubing section to allow enough time for the liquid to break up into droplets, as per the requisite of the two-phase cleaning method, before entering the passageway to be cleaned 400.

Air is supplied via air source 10 and directed to the inlet of the two-phase generating module 12 via pipe segments 126, 128, 130, 132, 134 and 136 through valve 46. Air flow is regulated by an air regulator 42, and monitored by a pressure gage 44, a pressure transducer 48 and a flow meter 50. These instruments provide a feedback loop to a controller 600.

The holding tank 14 is provided by first pumping means 30 via pipe segments 199, 198, 200, 202, 204, 205, 210, 212 and 214 through valves 84 and 76 at a pre-defined liquid pumping rate. Liquid pressure is monitored by a liquid pressure transducer 74. A return loop via pipe segments 209, 194, 192 and 193 through the manual valve 88 serves as a pressure adjustment means to maintain the desired pressure range necessary for operating the nozzle 13 in the two-phase generating module 12 during the cleaning period in order to avoid back pressure to other parts of the apparatus. The cleaning solution is then atomized/dispersed at the nozzle 13 and mixed with air to generate the two-phase cleaning mixture which is then directed to the inlet adapter 56 connected with the passageway to be cleaned 400 via pipe segments 138, 140, and 142 through valve 54. Thermocouple 52 is employed to measure the two-phase mixture temperature before entering the passageway to be cleaned 400. The two-phase exhaust leaving outlet adapter 58 connected to the passageway to be cleaned 400 is then directed to mist separator 500 via pipe segments 144, 146, 148 and 150 through valve 62. The exhaust pressure is monitored at pressure transducer 60. The liquid phase is then separated from the two-phase mixture inside the mist separator 500 and discharged via pipe 152 through valve 64, and gas is discharged via a ventilation duct 154. In this process the desired mixture temperature is controlled by the liquid heater 15 and air heater 11, and is monitored by the thermocouple 52 with a feedback loop to the controller 600.

If a second cleaning solution (such as an acidic solution) is required or desired in the second cleaning process, the cleaning solution is contained in a second cleaning solution holding tank 16. This cleaning solution is then supplied to the liquid inlet of the two phase generating module 12 by the first pumping means 30 via pipe segments 191, 190, 200, 202, 204, 205, 210, 212, and 214 through valves 84 and 76 at a pre-defined liquid flow rate. The liquid pressure is always monitored by the liquid pressure transducer 74. A return loop via pipe segments 209, 194, 188 and 189 through the manual valve 92 is used to serve as a pressure adjustment means to maintain the desired pressure range necessary for operating the nozzle 13 in the two-phase generating module 12. The cleaning solution is then atomized at the nozzle 13 and mixed with air to generate two-phase cleaning mixture which is then directed to the inlet adapter 56 which is connected with the passageway to be cleaned 400 via pipe segments 138, 140, and 142 through valve 54. A thermocouple 52 is employed to measure the two-phase mixture temperature before entering the passageway to be cleaned 400. The two-phase exhaust leaving outlet adapter 58, which is connected to the passageway to be cleaned 400, is directed to the mist separator 500 via pipe segments 144, 146, 148 and 150 through valve 62. The exhaust pressure is monitored with pressure transducer 60. The liquid phase is then separated from the two-phase mixture inside the mist separator 500 and discharged via pipe 152 through valve 64. A gas is discharged via a ventilation duct 154. In this process the desired mixture temperature is controlled by liquid heater 17 and the air heater 11 and monitored by the thermocouple 52.

Sanitizers can also be used after the cleaning step in many C-I-P operations. In this case, a sanitizer holding tank 18 is used to supply the sanitizing liquid. The sanitizer contained in the sanitizer holding tank 18 is supplied to the liquid inlet of the two phase generating module 12 by a second pumping means 32 via pipe segments 180, 182, 186, 187, 208 205, 210, 212 and 214 through valves 101 and 76 at a pre-defined liquid rate. Liquid pressure is monitored by the liquid pressure transducer 74. A return loop via pipe segments 184 and 185 through the manual valve 94 is used to serve as a pressure adjustment means to maintain a desired pressure range necessary for operating the nozzle 13 in the two-phase generating module 12. The sanitizing liquid is then atomized at the nozzle 13 and mixed with air to generate a two-phase sanitizing mixture which is then directed to the inlet adapter 56 which is connected with the passageway to be cleaned 400 via pipe segments 138, 140, and 142 through valve 54. A thermocouple 52 is employed to measure the temperature of the two-phase mixture before entering the passageway to be cleaned 400. The two-phase exhaust leaving the outlet adapter 58, which is connected to the system to be cleaned 400, is directed to the mist separator 500 via pipe segments 144, 146, 148 and 150 through valve 62. The exhaust pressure is monitored by pressure transducer 60. The liquid phase is then separated from the two-phase mixture inside the mist separator 500 and discharged via a pipe 152 through a valve 64 and air is discharged via a ventilation duct 154. In this process the desired two-phase mixture temperature is controlled by a liquid heater 19 and the air heater 11 and monitored by the thermocouple 52.

Sometimes water is mixed with air for rinsing purposes. In these cases, rinse water holding tank 20 is used to supply rinse water/liquid. Water is supplied to the liquid inlet of the two-phase generating module 12 by the third pumping means 34 via pipe segments 172, 174, 178, 206, 208, 209, 205, 210, 212 and 214 through valves 98 and 76. The liquid pressure transducer 74 is used to monitor water pressure. A return loop via pipe segments 176 and 177 through manual valve 96 is used to serve as a pressure adjustment means to maintain the desired pressure range necessary for operating the nozzle 13 in the two-phase generating module 12. Water is then atomized at the nozzle 13 and mixed with air to generate a two-phase rinsing mixture which is then directed to the inlet adapter 56 which is connected with the passageway to be cleaned 400 via pipe segments 138, 140 and 142 through valve 54. The thermocouple 52 is employed to measure the temperature of the two-phase mixture before entering the passageway to be cleaned. The two-phase exhaust leaving outlet adapter 58, which is connected to the passageway to be cleaned 400, is directed to the mist separator 500 via pipe segments 144, 146, 148 and 150 through valve 62. The exhaust pressure is monitored at pressure transducer 60. The liquid phase is then separated from the two-phase mixture inside the mist separator 500 and discharged via the pipe 152 through the valve 64, and gas or air is discharged via the ventilation duct 154. In this process the desired mixture temperature is controlled by a liquid heater 21 and an air heater 11 and monitored by the thermocouple 52.

In addition to the two-phase rinsing step discussed above, rinsing can also be accomplished by circulating water continuously through the passageway to be cleaned 400. In this step, a water source is supplied from the water holding tank 28 to the inlet adapter 56 which is connected to the system to be cleaned by the sixth pumping means 40 via pipe segments 231, 230, 234, 246, 250, 270, 272, 140 and 142 through valves 114, 106 and 54. The water flow rate is monitored using a flow meter 120. Instead of using the water from water holding tank 28, water can also be supplied from an outside source to the water holding tank 28 via pipe segments 254 and 252 through a valve 124. After passing through the passageway to be cleaned 400, the rinse water is directed to the adapter 58 and to the mist separator 500 via pipe segments 144, 146, 148, and 150 through valve 62. The rinse water inside the mist separator 500 is then discharged via a pipe segment 152 through valve 64. In many cases, warm or hot water can enhance cleaning results and thus controlling the rinse water temperature becomes important in the control of the process. This can be achieved by using a heater and its controller 29 inside the water holding tank 28.

Rinsing with water is enhanced by applying intermittent air pulsation can increase rinsing effectiveness. This step is achieved by applying a continuous supply of water as described above and intermittently introduces pressurized air to the rinse water stream. Air is supplied from the air source 10 to the valve 54 to push the rinse water through the passageway to be cleaned 400 via pipe segments 126, 128, 130, 132, 134, 136, 138, 140 and 142 through valve 46 and the two-phase generating module 12. The air is regulated by the regulator 42 and monitored by pressure gage 44, pressure transducer 48 and flow meter 50. During this process, valves 70 and 76 are closed to avoid any back pressure to other parts of the apparatus. The pulsation pattern is controlled by the valve 46 which is electronically controlled by the controller 600. A typical pattern of the pulsation is to open the valve 46 for about 3-6 seconds after every 6-10 seconds. With the automatic control from the controller 600, other pulsation patterns can be easily achieved.

Re-circulation of the cleaning solution, sanitizer or rinse water through the passageway to be cleaned 400 for a period of time with a desired liquid temperature is an important step for soaking or rinsing the internal surfaces of passageways or equipment in processing industries. In this step, liquids are circulated through the system to be cleaned with a continuous liquid phase. When the first cleaning solution, which may be a basic solution, is applied for re-circulation purposes, the cleaning solution contained in the cleaning solution holding tank 14 is pumped to the inlet adapter 56 by the fourth pumping means 36 via pipe segments 227, 226, 228, 266, 268, 270, 272, 140 and 142 through the valves 87, 102 and 54. The liquid flow rate is monitored by the flow meter 120 and the temperature of the liquid is monitored by the thermocouple 52. After passing through the passageway to be cleaned 400, the cleaning solution leaves the system to be cleaned at the outlet adapter 58 and is directed to the cleaning solution recirculating tank 22 via pipe segments 144, 146, 148, 264, 262, 260, and 261 through valves 62 and 116. The liquid pressure transducer 60 is used to monitor the liquid pressure during the process. This process is continued until the liquid level in the cleaning solution recirculating tank 22 reaches about 80%, when the circulation process does not consume more fresh cleaning solution from the cleaning solution holding tank 14. At this moment, valve 87 is closed and valve 108 is opened so that the cleaning solution retained in the cleaning solution recirculating tank 22 is connected to the above mentioned recirculation loop via pipe segments 241, 240 and 236 through the valve 108. The recirculation process is then continued for a period of time depending on rinsing or soaking requirements for each cleaning process/protocol. The desired liquid temperature is controlled by a heater 15 before the valve 87 is closed and by a heater 23 throughout the entire recirculation process.

When the second cleaning solution (here referred as acidic solution) is required for recirculation purposes, the cleaning solution contained in the cleaning solution holding tank 16 is pumped to the inlet adapter 56 by the fourth pumping means 36 via pipe segments 223, 222, 224, 228, 266, 268, 270, 272, 140 and 142 through valves 91, 102, and 54. The liquid flow rate is monitored by the flow meter 120 and the temperature of the liquid is monitored by the thermocouple 52. After passing through the passageway to be cleaned 400, the cleaning solution exits at the outlet adapter 58 and is directed to the cleaning solution recirculating tank 24 via pipe segments 144, 146, 148, 264, 262, 258, and 259 through valves 62 and 118. A liquid pressure transducer 60 is used to monitor the liquid pressure during the process. This process is continued until the liquid level in the cleaning solution holding tank 24 reaches about 80% when the circulation process does not consume more fresh cleaning solution from the cleaning solution holding tank 16. The valve 91 is closed and valve 110 is opened so that the cleaning solution retained in the cleaning solution recirculating tank 24 is connected to the above mentioned recirculation loop via pipe segments 239, 238 and 236 through valve 110. The desired liquid temperature is controlled by heater 17 before valve 91 is closed and by heater 25 throughout the entire recirculation process.

When a sanitizer is required for recirculation purposes, the sanitizer solution contained in the sanitizer holding tank 18 is pumped to inlet adapter 56 by the fifth pumping means 38 via pipe segments 217, 216, 218, 220, 242, 250, 270, 272, 140 and 142 through valves 95, 102 and 54. The liquid flow rate is monitored by flow meter 120 and the liquid temperature is monitored by the thermocouple 52. After passing through the passageway to be cleaned 400, the sanitizer exits the passageway at outlet adapter 58 and is directed to the sanitizer recirculating tank 26 via pipe segments 144, 146, 148, 264, 263 and 256 through valves 62 and 122. The liquid pressure transducer 60 is used to monitor the liquid pressure during the process. This process is continued until the liquid level in the sanitizer recirculating tank 26 reaches about 80% when the circulation process does not consume more fresh sanitizer from the sanitizer solution holding tank 18. The valve 95 is then closed and the valve 112 is opened so that the sanitizer retained in the sanitizer recirculation tank 26 is connected to the above mentioned recirculation loop via pipe segments 233 and 232 through the valve 112. The recirculation process is then continued for a period of time depending on rinsing and soaking requirements of each sanitizing case. A desired liquid temperature is controlled by heater 19 before valve 95 is closed and by the heater 27 throughout the entire recirculation process.

Figure 3:
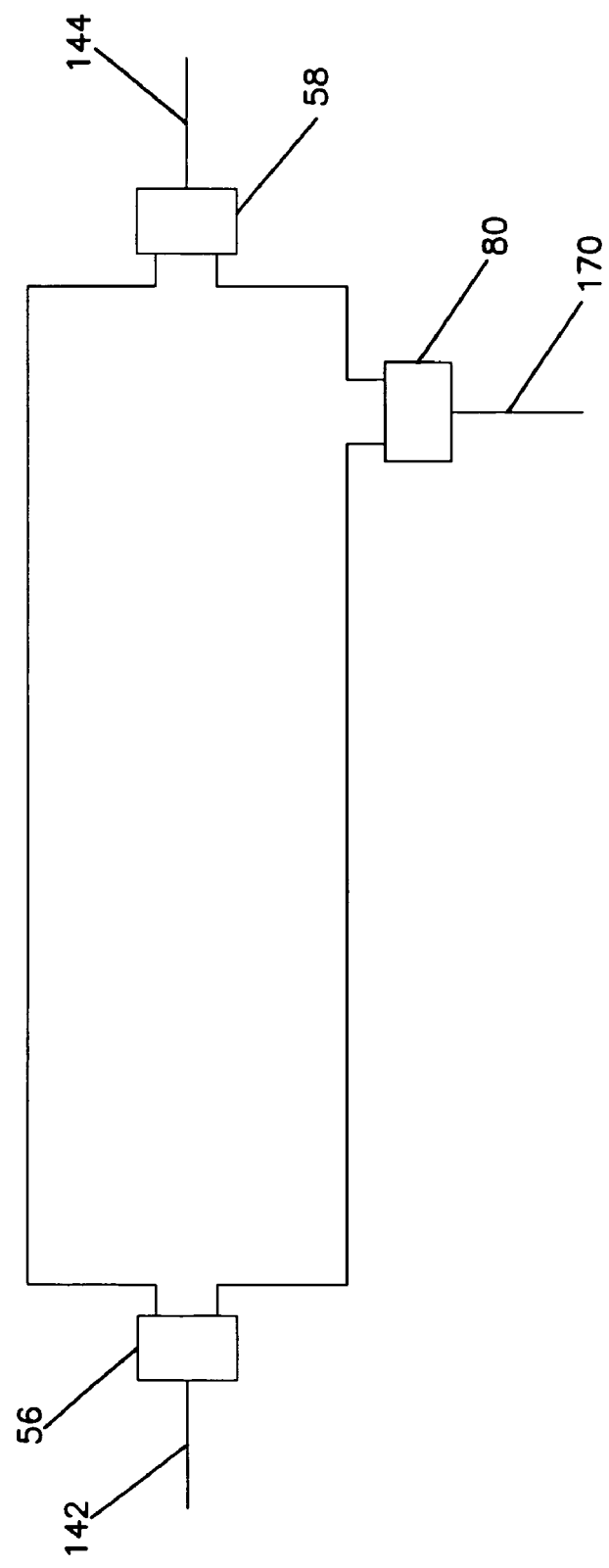
FIG. 3 is a cross sectional view of a membrane system with backflushing means to be used with the two-phase flow.

Backflushing is an important option of the two-phase cleaning apparatus 100, used particularly to clean tubular and hollow fiber membranes where backflushing is often required, for instance for ultrafiltration and microfiltration separation membranes. Backflushing usually involves the use of either a cleaning solution or water in liquid phase, or in the form of the two-phase mixtures in other cases. In this step, a second liquid inlet adapter 80 is used to connect the backflushing fluid to the product port of the membrane to be cleaned, as shown in FIG. 3. When the backflushing is in the form of a cleaning solution in a liquid phase or foam mixture, the cleaning solution in the cleaning solution holding tank 14 is delivered to inlet adapter 80 by the first pumping means 30 via pipe segments 199, 198, 200, 202, 204, 205, 168, and 170 through valves 86, 84 and 78. Meanwhile air is supplied from the air source 10 via pipe segments 158, 160, 162, 164, and 166 to pipe 210 to pressurize the liquid that is held inside the housing of the membrane to be cleaned 400. Air in this case is regulated by the regulator 66 and monitored by the pressure gage 68 and pressure transducer 72. A liquid return loop via pipe segments 209, 194, 192, and 193 through the manual valve 88 is used to adjust the liquid pressure within a range that can be sustained by the membrane housing. Any permeate generated during this backflushing operation is directed to the mist separator 500 via pipe segments 144, 146, 148, and 150 through valve 62. The liquid collected inside the mist separator 500 is then discharged via pipe segment 152 through valve 64. This process can be performed at the desired liquid and air pressures depending on the specifications of the membrane to be cleaned.

If an air stream is introduced to the lumen of tubular or hollow fiber membranes during back flushing, a two-phase flow can be formed in situ and can be used to clean the lumen side of the membrane and thus enhance overall cleaning. This in situ two-phase generation step is achieved in apparatus 100 by introducing air to the inlet adapter 56 which is connected to the inlet of the membrane to be cleaned 400 via pipe segments 126, 128, 130, 132, 134, 136, 138, 140 and 142 through valves 46 and 54 and the two-phase generating module 12. Air in this case is regulated by the regulator 66 and monitored by the pressure transducer 72. With two-phase flow generated in situ, the mist separator 500 is collecting two-phase exhaust rather than liquid phase only. Liquid is separated from the two-phase exhaust inside the mist separator 500 and discharged via pipe segment 152 through valve 64 and air is discharged via pipe segment 154.

If a second cleaning solution in the form of a liquid phase or as a foam mixture is needed for backflushing purposes, the cleaning solution in the cleaning solution holding tank 16 is delivered to the inlet adapter 80 by first pumping means 30 via pipe segments 191, 190, 200, 202, 204, 205, 168, and 170 through valves 90, 84, and 78. Meanwhile air is supplied from the air source 10 via pipe segments 158, 160, 162, 164, and 166 to pipe 210 for use to pressurize the liquid that is held inside the membrane housing. Air in this path is regulated by the regulator 66 and monitored by the pressure gage 68 and the pressure transducer 72. A liquid return loop via pipe segments 209, 194, 188 and 189 through manual valve 92 is used to adjust the liquid pressure within a range that can be sustained by the membrane housings. Any permeate liquid formed inside the membrane lumen during the backflushing step is directed to the mist separator 500 via pipe segments 144, 146, 148, and 150 through valve 62. The liquid collected inside the mist separator 500 is then discharged via pipe segment 152 through valve 64. This process can be performed under certain desired liquid and air pressures, depending on the specification of the membrane to be cleaned.

As discussed above, if an air stream is introduced to the lumens of the tubular or hollow fiber membranes by backflushing, a two-phase flow can be created in situ inside the lumen of the membrane to enhance the cleaning surface of the membrane. This step is again done by introducing air to inlet adapter 56 via pipe segments 126, 128, 130, 132, 134, 136, 138, 140, and 142 through valves 46 and 54 and the two phase generating module 12. Air in this path is regulated by regulator 66 and monitored by pressure transducer 72. With the two-phase generated in situ, the mist separator 500 is collecting two-phase exhaust rather than liquid phase only. Liquid is separated from the two-phase exhaust inside the mist separator and discharged via pipe segment 152 through valve 64 and air is discharged via pipe segment 154.

If a sanitizer is used in the backflushing process as required for pharmaceutical and medical facilities, the sanitizer in the sanitizer holding tank 18 is delivered to inlet adapter 80 by the second pumping means 32 via pipe segments 180, 182, 186, 187, 208, 209, 205, 168 and 170 through valves 100 and 78, meanwhile air is supplied from the air source 10 via pipe segments 158, 160, 162, 164, and 166 to pipe 210 for use to pressurize the liquid that is held inside of the membranes. Air in this path is regulated by the regulator 66 and monitored by the pressure gage 68 and pressure transducer 72. A liquid return loop via pipe segments 184 and 185 through manual valve 94 is used to adjust liquid pressure within a range that can be sustained by tubular membrane housing. Any permeate liquid generated during backflushing into the lumens of the membrane is directed to mist separator 500 via pipe segments 144, 146, 148, and 150 through valve 62. The liquid collected inside a mist separator 500 is then discharged via pipe segment 152 through valve 64. This process can be performed under certain desired liquid and air pressures depending on the specifications of membrane housing design.

As discussed above, the backflushing process can be used to supply liquid to the lumen side of the membrane and a two-phase flow can be generated in situ when mixed with air directed to the lumen side from the air source 10. This step is done by introducing air to the inlet adapter which is connected to the inlet of the membrane to be cleaned via pipe segments 126, 128, 130, 132, 134, 136, 138, 140, and 142 through valves 46 and 54 and the two-phase generating module 12. Air in this pass is regulated by the regulator 66 and monitored by the pressure transducer 72. With the two phase mixture generated in situ, the mist separator 500 is collecting two-phase exhaust rather than liquid phase only. Liquid is separated from the two-phase exhaust inside the mist separator 500 and discharged via pipe segment 152 through valve 64 and air is discharged via pipe segment 154.

If water is to be used in the backflushing process during membrane cleaning processes, water in the holding tank 20 is delivered to inlet adapter 80 by the third pumping means 34 via pipe segments 172, 174, 178, 206, 208, 209, 205, 168 and 170 through valves 98 and 78. Meanwhile and simultaneously, air is supplied from the air source 10 via pipe segments 158, 160, 162, 164 and 166 to the pipe 210 for use to pressurize the liquid that is held inside the housing of the membrane. Air in this path is regulated by the regulator 66 and monitored by the pressure gage 68 and the pressure transducer 72. A liquid return loop via pipe segments 176 and 178 through a manual valve 98 is used to adjust the liquid pressure within a range that can be sustained by the membrane. Any permeate liquid created inside the lumen of the membrane is directed to the mist separator 500 via pipe segments 144, 146, 148, and 150 through the valve 62. The liquid collected inside the mist separator 500 is then discharged via pipe segment 152 through valve 64. This process can be performed under certain desired liquid and air pressures depending on the specifications of the membrane to be cleaned.

As discussed above, a two-phase flow can be created, in situ, in the membrane lumen by mixing the backflushing liquid with air from the air source 10. The gas to liquid ratio in this case is adjusted by controlling the backflushing liquid and air pressures. This step is done by introducing air to the inlet adapter which is connected to the inlet of the membrane to be cleaned via pipe segments 126, 128, 130, 132, 134, 136, 138, 140, and 142 through valves 46 and 54 and the two phase generating module 12. Air in this path is regulated by the regulator 66 and monitored by the pressure transducer 72. With the two-phase flow generated in situ in this case, the mist separator 500 is collecting two-phase exhaust rather than liquid phase only. Liquid is separated from the two-phase exhaust inside the mist separator 500 and discharged via pipe segment 152 through valve 64; air is discharged via pipe segment 154.

The drying step is an important part of the apparatus 100. It allows dry air that is heated to a desired temperature by heater and controller 11 to pass through the internal surfaces of the passageway to be cleaned 400. Drying is usually performed after the cleaning, sanitizing and rinsing steps to prevent bacterial growth or biofilm formation. Drying is done by introducing dry air at the desired temperature from the air source 10 to the adapter that is connected with the inlet of the object to be cleaned via pipe segments 126, 128, 130, 132, 134, 136, 138, 140 and 142 through valves 46 and 54 and the two-phase generating module 12. Air is regulated by the regulator 42 and monitored by the pressure gage 44, pressure transducer 48 and the flow meter 50. The air temperature is also monitored by the thermocouple 52. The air leaving the system to be cleaned at the adapter 58 is directed to the mist separator 500 via pipe segments 144, 146, 148, 150 through the valve 62. The transducer 60 is used to monitor the pressure of the exhaust. Air is then discharged via pipe segment 154 from the mist separator 500. Any liquid collected during the drying process is discharged via the pipe segment 152 through the valve 64.

The controller unit 600 is a PLC-operated controller. It is programmed to operate all control valves, pumps, heaters and their controllers, pressure transducers, and flow meters in accordance with a designed operating sequence to carry out all the function discussed above. All the components that are connected to the controller 600 are displayed in FIG. 1 with an electrical contact symbol.

Valve 82 and pipe segment 156 provides means for collecting water or liquid samples during each step of the process to monitor the quality of the rinse water, the cleaning agent concentration, and the sanitizing agent concentration. The collected samples are used to monitor pH, conductivity, surfactant concentration, and sanitizer concentration such as bleach, peroxy-acids, iodine or others. The liquid temperature is normally monitored at the thermocouple 52.

In another variation of the apparatus, liquids discharging from the mist separator 500 through the valve 64 can be connected through a pipe 196 to the manifold 263 and also recirculated back to the corresponding tank or pump to be fed again to the system to be cleaned.

FIGS. 2A, 2B and 2C illustrate alternate equipment used to create a two-phase flow.

FIG. 2A illustrates generating droplets using a nozzle 13. A gas inlet pipe 136 and a liquid pipe 214 mix the two phases in the two-phase generating module 12. The two-phase flow exits in pipe 138.

FIG. 2B illustrates generating droplets using a liquid delivery orifice 31, which is at an angle with respect to the gas inlet pipe 136. After mixing the air and liquid, the mixture again exits in pipe 138.

FIG. 2C illustrates generating droplets using a T arrangement of the liquid inlet pipe 214 which is about perpendicular with the gas inlet pipe 136. The two-phase mixture exits through pipe 138.

FIG. 3 illustrates a system 400 that can be used to backflush the liquid-air mixture.

A pipe 142 is used to inlet the air-fluid mixture through inlet adapter 56. A pipe 170 feeds a backflushing liquid into the passageway 400 via an inlet adapter 80. When backflushing is complete, the mixture exits through the outlet adapter 58 via the pipe 144.

Figure 4:
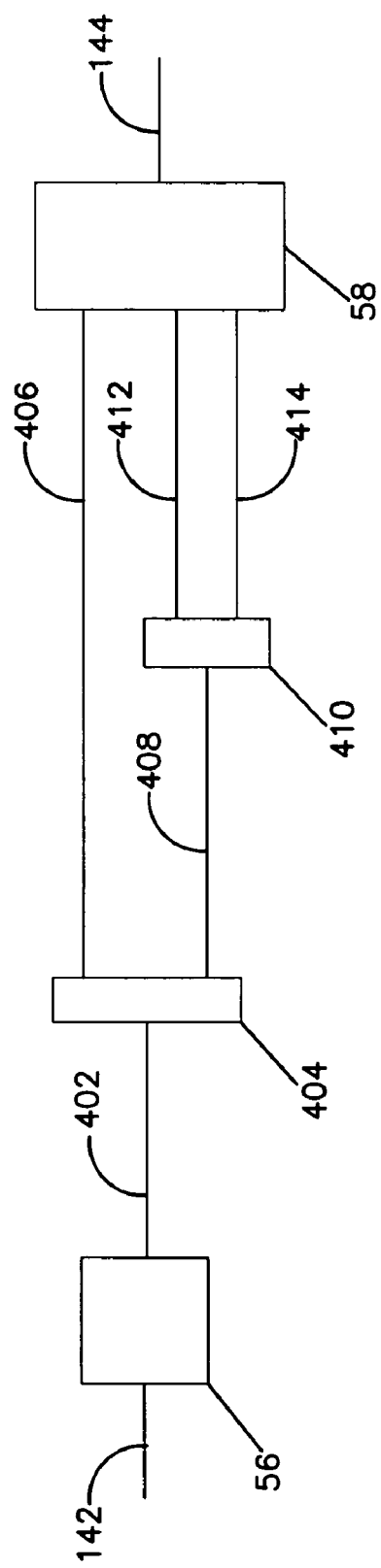
FIG. 4 is a cross sectional view of a pipe distribution network that can be cleaned using two-phase flow.

FIG. 4 illustrates a pipe distribution network 400 to be cleaned. Air and liquid in a pipe 142 are combined in an inlet adapter 56 and flows through pipe 402 to be cleaned through a bifurcation valve 404. This valve 404 in turn connects to two pipes to be cleaned, 406 and 408/In turn, pipe 408 flows through a second bifurcation valve 410 to clean pipes 412 and 414. The mixture exits through outlet adapter 58 via a pipe 144.

Figure 5:
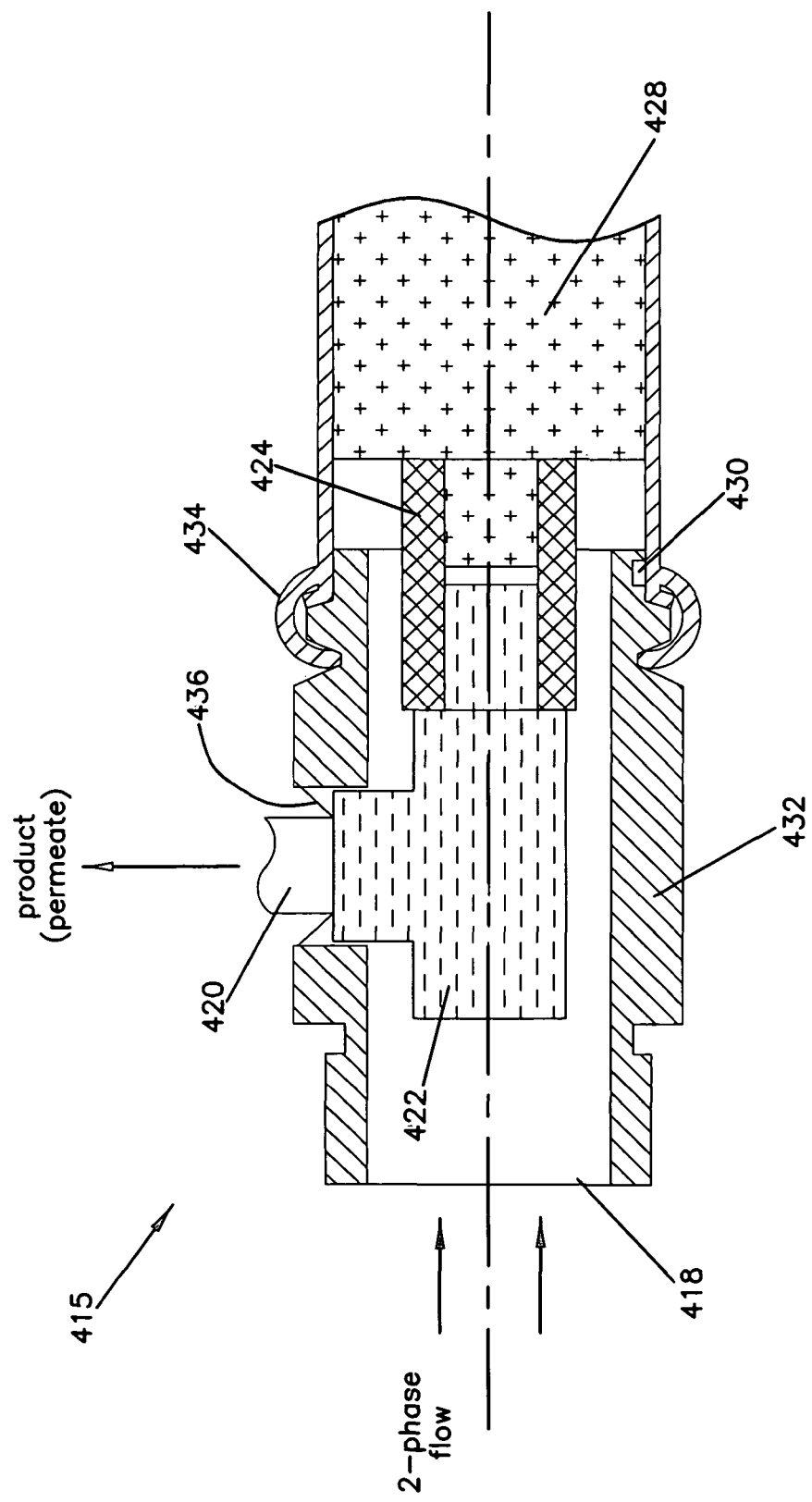
FIG. 5 is a cross sectional view of an adapter used to separate feeding channels from permeate channels of membranes during two-phase flow cleaning.

FIG. 5 is a cross sectional view of an adapter used to clean membrane channels-using two phase flow cleaning.

The invention will be further described in the following Examples. However, the invention is not meant to be limited by the details described therein. In the Examples, the apparatus parts refer to FIG. 1.

Example 1

This example describes apparatus and process for removing biofilm, contaminants and debris from passageways that carry pure water or bicarbonate dialysate solution as used in dialysis center water systems, pharmaceutical plants or industrial operations that require the use of pure water distribution systems. To simulate the above water distribution systems, we constructed a water system that allowed us to grow biofilm on the lumen surface of long tubing having a range of internal diameters by circulating water or other liquids suitable for biofilm growth. In this example, the passageway to be cleaned was constructed from PVC tubing and pipes having internal diameters from 0.25 inch to 1 inch, and having lengths from 100 to 300 feet. This arrangement provides pipelines and tubing with a length to diameter (L/D) ratio between 1,000 and 15,000. The tubing and pipe used to construct this arrangement were made from clear PVC to allow us to observe the two-phase flow at any section along the pipe. This pipe arrangement is referred to as a pipe system hereafter.

After allowing biofilm to grow for several weeks, we subjected these simulated pipes to two-phase cleaning for five or ten minutes, and measured both water quality (CFU/ml) and biofilm density (CFU/cm$^2$) before and after the two-phase flow cleaning. SEM was also used to evaluate biofilm before and after the application of the two-phase flow cleaning for one set of experiments. All the cleaning was done with a two-phase mixture where the liquid phase contained sodium hydroxide to a pH about 11.5 or higher. This solution is safe and is currently recommended for cleaning dialysis water systems. A high pH condition lowers the adhesive strength of biofilm to PVC tubing surfaces, and facilitates its removal with the two-phase dynamics.

Part A

The above pipeline system was connected as the passageway to be cleaned 400 in apparatus 100. The inlet of the pipeline system was connected to an inlet adapter 56 and its outlet was connected to an outlet adapter 58. Cleaning of the pipeline system was performed using a two phase flow mixture generated inside the two phase generating module 12 by supplying air from air source 10 through line segments 126, 128, 130, 132, 134 and 136 which connect to the inlet of the two phase generating module 12. The air flow rate was controlled by pressure regulator 42 and air flow meter 50 and monitored by pressure gauge 44 and pressure transducer 48. The cleaning solution used to form the two phase flow mixture was supplied from cleaning solution holding tank 14 through a valve 86 using first pumping means 30 through line segments 199, 198, 200, 202, 204, 210, 212 and 214 leading to the liquid inlet of the two-phase generating module 12. The liquid flow rate was controlled by adjusting the first pumping means 30 and was monitored by pressure transducer 74. During cleaning, air was supplied to the inlet of the two phase generating module 12 by opening a valve 46, and the cleaning solution was supplied at the required flow rate by first pumping means 30 by opening valves 84 and 76. The liquid was supplied to the two-phase generating module 12 via a nozzle P-type Fine Atomization Nozzle made by Bete Fog Nozzle, Inc. of Greenfield, Mass. This nozzle provides droplet sizes in the range of 25 to 400 microns. When the liquid droplets are mixed with air inside the two-phase generating module 1Z, they form a two phase flow that was directed to the pipeline system by opening valve 54 through the inlet adapter 56. The two-phase flow passes through the pipeline system 400 and exits through the outlet adapter 58 to a mist separator 500 through line segments 144, 146, 148 and 150 by opening a valve 62. The discharged two-phase flow mixture is separated into a gas stream that is vented through an outlet 154 and the liquid phase is discharged through line segment 152 through a valve 64. After the cleaning step, the pipe system 400 was rinsed with a two-phase flow mixture consisting of water and air, supplied through the two-phase generating module 12. The air supplied to the two-phase generating module 12, was supplied in the same way as described above for the cleaning step. Rinse water was supplied from rinse water holding tank 20 and pumped through a third pumping means 34 via line segments 172, 174, 178, 206, 208, 209, 210, 212 and 204, which connects to the liquid inlet of the two-phase generating module 12. The two phase flow generated in the two phase generating module 12 is directed to the pipeline system 400 for rinsing, and discharged through the outlet 58 to the mist separator 500, where the air and water are separately discharged through ports 154 and 152 respectively. During rinsing, the same air pressure was used as in the cleaning step, and the rinse water flow rate was between 15 to 200 ml/min. During rinsing, the optimal time was about 10 minutes and was determined by monitoring the pH and specific conductivity of the rinse liquid by withdrawing rinse liquid from the test port 82. Rinsing was continued until the rinse liquid had the same pH and specific conductivity as the water supplied from the rinse water holding tank 20.

Part B

Rinsing was done using a continuous flow of pure water from a pure water source 254 or the rinsing water recirculating tank 28 via a sixth pumping means 40 through line segments 231, 230, 234, 242, 246, 250, 270 and 272 through a valve 54 and the inlet adapter 56. The rinse solution was discharged through the outlet adapter 58 via line segments 144, 146, 148 and 152 through a valve 62.

Part C

In another experiment, the rinsing was done using a pulsing mode. In this case, a continuous supply of water from the water source 254 or the rinse water recirculating tank 28 was delivered by the sixth pumping means 40 through line segments 231, 230, 234, 242, 246, 250, 270 and 272 through the valve 54 and the inlet adapter 56. In this rinsing mode, the air was supplied intermittently for 3 seconds after every six seconds of a continuous liquid flow, by opening valve 46 with the aid of the control system 600. The rinse time in these cases was again determined by the same method, by measuring the pH and the specific conductivity of the rinse solution from the sampling port 82. The discharge of rinse liquid in this case was the same as described above.

The cleaning parameters used to remove biofilm from the pipeline system 400 were: a) the inlet air pressure to the two phase generating module 12 was regulated at 30-50 psig; b) the cleaning solution flow rate to the inlet of the two phase generating module 12 was 15-100 ml/min; c) the estimated velocity at the inlet of pipeline system 400 was in the range of 48-104 ft/sec; d) the estimated exit velocity at the adapter 58 was in the range of 114-390 ft/sec; and e) the liquid to gas ratio used to clean pipeline system 400 was in the range of 1/800 to 1/14000.

The results of biofilm removal from 0.25 and 0.5 inch diameter tubing, each 100 feet long, are set forth in Table 1 below:

TABLE 1

| Tubing | D (in) | L/D | Biofilm Age (weeks) | Cleaning Time (min) | Velocity (ft/s) In | Velocity (ft/s) Out | Liquid/Air Ratio (volumetric) In | Liquid/Air Ratio (volumetric) Out | CFU/cm² Pre | CFU/cm² Post |
|---|---|---|---|---|---|---|---|---|---|---|
| S2 | 0.25 | 4800 | 2 | 5 | 75 | 345 | 1/860 | 1/4000 | 890 | <10 |
| S3 | 0.25 | 4800 | 2 | 10 | 75 | 345 | 1/860 | 1/4000 | — | <10 |
| B1 | 0.50 | 2400 | 2 | 10 | 48 | 114 | 1/1400 | 1/3300 | 550 | 30 |
| S4 | 0.25 | 4800 | 4 | 10 | 72 | 360 | 1/800 | 1/4100 | $1.8 \times 10^5$ | <1 |
| S5 | 0.25 | 4800 | 4 | 5 | 90 | 390 | 1/1000 | 1/4400 | $1.8 \times 10^5$ | <1 |
| B2 | 0.50 | 2400 | 4 | 10 | 69 | 186 | 1/2000 | 1/5400 | $6.2 \times 10^5$ | <10 |

These results show that water in contact with a biofilm-laden surface before cleaning can have over one million CFU/ml in the case of two week old biofilm. After either 5 or 10 minutes of two-phase cleaning, both the surface of the tubing and distilled water stored in the tubing demonstrate that effective cleaning gas been achieved.

The results further show that during 4 weeks of exposure to tap water, the biofilm density has increased to the order of 100,000 CFU/cm².

After cleaning, the biofilm density was reduced to almost zero, and the bacterial counts reflect this.

Figure 6A:
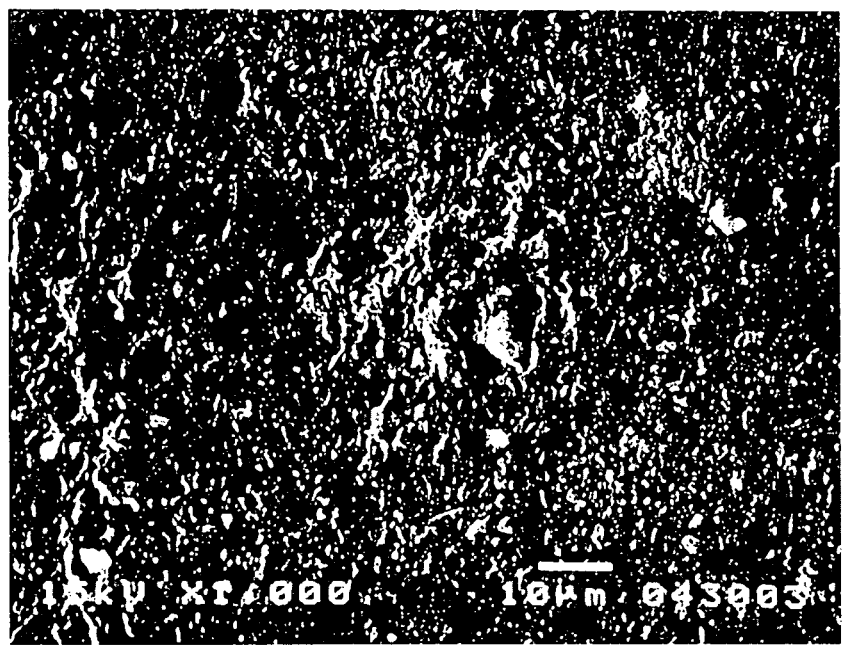
FIG. 6A is a photomicrograph of a lumen surface of a pipe prior to cleaning.
Figure 6B:
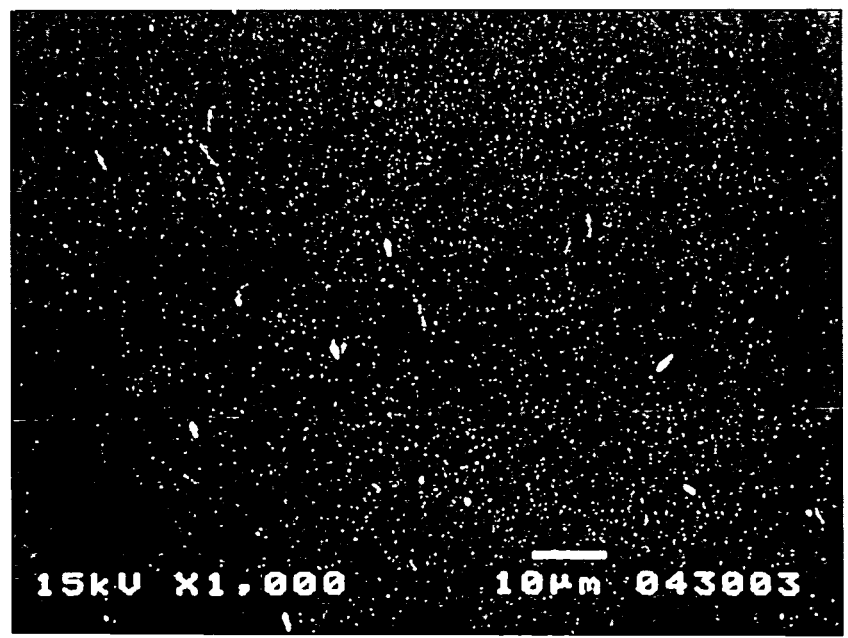
FIG. 6B of a photomicrograph of a lumen surface of a pipe after cleaning with the present two-phase method.

The above microbiology results have been supported by SEMs on the surface of the tubing before and after cleaning—see FIGS. 6A & 6B. It is clear from the SEM of FIG. 6A that a mature biofilm with extensive polysaccharide matrix has formed at the surface of the tubing. Two-phase flow cleaning achieves significant removal of the biofilm along with its associated matrix, as shown in FIG. 6B.

Example 2

This example describes the process for removing biofilm and residues from tubing that carry carbonated water or beverages such as those used in soda fountain and beverage dispensing machines.

A flow of water was maintained through a ⅜ inch internal diameter plastic tubing having a length of 50 feet (L/D=1600) for three months to simulate soda fountain conditions in the field. A thick biofilm formed on the tubing during this period of time.

The tubing was cleaned using the apparatus of FIG. 1 and an alkaline cleaning agent including 0.1% of Tergitol-1X surfactant having a pH of 11.5 for five minutes. The liquid to gas ratio was 1:1800 and the pressure was 45 psig. Air velocities at the inlet and the outlet of the tube were 50 ft/sec and 250 ft/sec, respectively.

Complete removal of the biofilm from the entire length of the tubing was obtained, as measured by standard microbiology methods. Thus the shear stress of the two-phase flow was high enough to overcome the biofilm adhesion having an adhesive strength of about 100 Pascals. This tubing arrangement is referred to as soda or beverage line and was cleaned by apparatus 100 as in Example 1.

The cleaning conditions that were found to completely remove biofilm from soda and beverage line were: a) air pressure, 40-50 psig; b) liquid to gas ratio, 1/1400 to 1/7300; c) gas velocities, 70-360 ft/sec; d) the cleaning solution used to create the two phase flow included a non-ionic surfactant like Tergitol-1X made by Dow Chemical Co and it had a pH between 10.5-13.0; e) cleaning time, 10 min; f) rinsing time, 5 min.

The CFU/cm² showed an initial count of $1.8 \times 10^5$ CFU/cm² before cleaning and <1 CFU/cm² after the two phase cleaning performed as described above. SEM micrographs confirmed the effective removal of biofilm including the polysaccharide matrix from the soda and beverage line used in this example. Furthermore, the use of a high pH cleaning solution in the above range was found to be essential to remove biofilm from soda or beverage lines. We found that cleaning solutions in the acid pH range were ineffective to remove biofilm within a reasonable period of time.

Example 3

This example illustrates the use of apparatus 100 and the two-phase process to remove biofilm and residue from small tubing having an internal diameter between 1.2 to 2 mm and lengths up to 5 meters, with a range of L/D from 2500 to 4000. In this case, the object to be cleaned includes a network of lines as depicted in FIG. 4. This network of lines is referred to as a distribution network in this example and illustrates the use of apparatus 100 in cleaning a network of lines where there is branching and more than one line in the distribution network.

Referring to FIG. 4, the distribution network has a common inlet line 402, a 3-way valve 404 when the line 402 divides into two lines 406 and 408. Line 408 has a 3-way valve 410, which then splits into two lines 412 and 414. This network of lines became contaminated with biofilm and residues due to the flow of water or like liquids. This kind of arrangement is common in industrial applications such as food and beverage processing, and in medical devices such as in dental chairs and dialysis machines.

A network of lines used in a dental chair in use for 11 years was cleaned using apparatus 100. A base line bacterial count was performed for a period of seven weeks. The network was found to be highly contaminated with mature biofilm. The bacterial level in water passing through this line had a range between $10^6$-$10^7$ CFU/ml. This network was cleaned with the two-phase flow process using apparatus 100 as follows:

The inlet of the distribution network 400 shown in FIG. 1 was connected to inlet adapter 56 which directs the two phase flow mixture through the distribution network. The outlet of lines 406, 412, and 414 are collectively connected to outlet adapter 58 for the purpose of discharging the two-phase flow through the mist separator 500. The two-phase flow delivered to the adapter 56 is formed using the same arrangement as described in Example 1 with the aid of controller 600. In this network, the following steps were used to clean, rinse and sanitize. The two-phase flow conditions used in this example were: a) air pressure, 40-80 psig; b) liquid to gas ratio, 1/1500; and c) cleaning/sanitizing/disinfecting solution flow rate, 5 to 10 ml/min.

Step 1—Air purge: The distribution network was first purged with air supplied from the air source 10 through the regulator 42 and the control valve 46 for 30 seconds. The discharged mixture was directed to the mist separator as described in Example 1.

Step 2—Two phase cleaning/sanitization/disinfection: a) Two phase flow was created in the two phase generating module 12 and delivered through the inlet adapter 56 to clean lines 402 and 406 together for 90 seconds via the control valve 404; b) The two phase flow from the inlet adapter 56 was used to clean lines 402, 408 and 412 via control valves 404 and 410 for 90 seconds; c) The two phase flow from the inlet adapter 56 was used to clean lines 402, 408 and 414 via control valves 404 and 410 for 90 seconds. The cleaning/sanitizing/disinfecting solution included a mixture of a non-ionic surfactant and a biocide. The pH was 10.5-13.0.

Step 3—Rinsing with pulsation: The rinsing was performed in the pulsing mode as described in Example 1—Part C as follows: Pure rinse water was supplied from rinse water source 254, or rinsing water recirculating tank 28, through line segments 230, 234, 242, 246, 250, 270 and 272 via valve 54 to inlet adapter 56 in a continuous mode. During rinsing, air was injected intermittently for 3 seconds after every 6 seconds. The lines were rinsed in the same sequence as in the cleaning step described above.

Step 4—Rinsing with continuous water flow: Rinsing in this step was performed with a continuous flow of water supplied from the rinse water source 254 or rinsing water recirculating tank 28 through the sixth pumping means 40 without the use of air. In this step all the lines were rinsed together by opening the valves 404 and 410 for 120 seconds.

The quality of rinse water was tested by collecting water samples through port 82 by measuring pH, specific conductivity and surfactant concentration.

Step 5—Purging and drying: In this step, the network distribution system was purged with air supplied from the air source 10 through the adapter 56 for 60 seconds. This step minimizes biofilm growth during periods of non-use of the tubing.

Figure 7A:
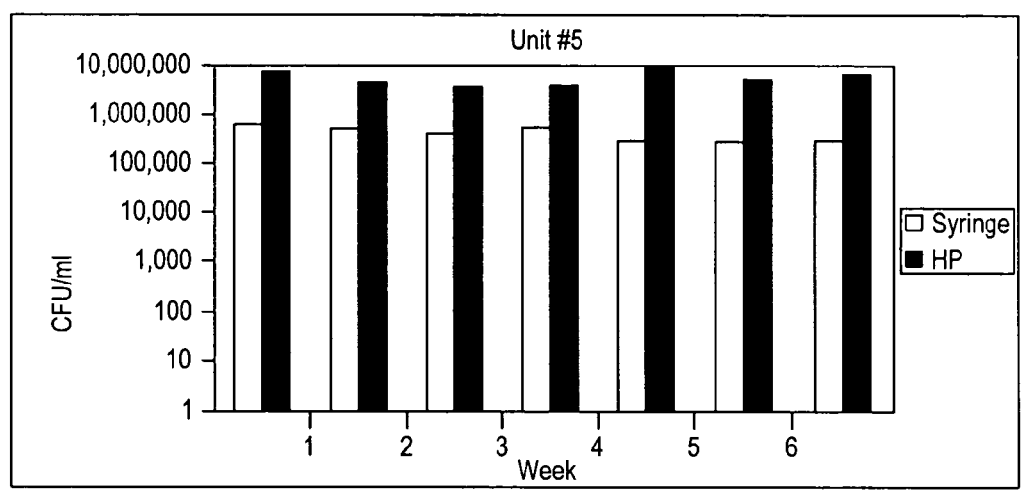
FIG. 7A is a graph of bacteria count in CFU/ml collected over several weeks prior to two-phase cleaning.
Figure 7B:
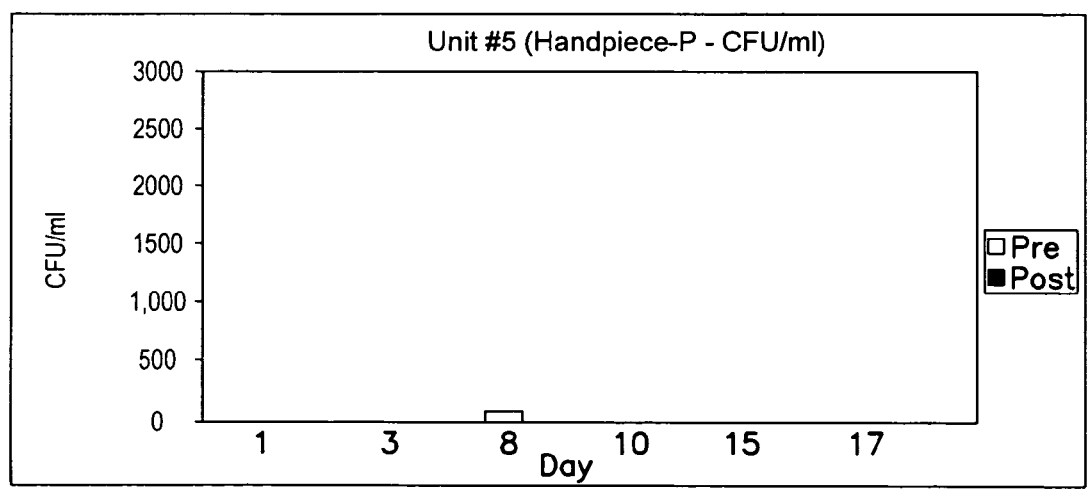
FIG. 7B is a graph of bacteria count in CFU/ml as monitored for some days after two-phase cleaning.

The use of this cleaning and sanitizing mechanism achieved complete removal of biofilm as shown by SEM analysis and bacterial counts taken for over a period of 3 months. The results are shown in FIGS. 7A and 7B.

Example 4

This example describes a process and apparatus for removing bio burden and pathogens from medical tubing such as those used in endoscopes, catheters, surgical drainage tubes, respirators, ventilators and the like. Two 3-meter long plastic tubings having internal diameters of 1.1 mm and 4 mm respectively, were contaminated with Bacillus subtilis spores in British soil (i.e. 10 ml of Bovine serum, 10 ml of saline solution and 6 grams of dry milk powder) at a level of $1.6 \times 10^6$ CFU/tubing and were allowed to dry overnight to ensure that the soil became highly adherent to the lumen surface of the tubing. These contaminated tubings were separately connected to apparatus 100 through the inlet adapter 56 and the outlet adapter 58. Two phase flow was generated in the two phase generating module 12 by supplying air from the air source 10 to the gas inlet of the two phase generating module 12 as described in Example 1. An alkaline cleaning solution (pH=11.5) and a non-ionic surfactant, Tergitol-1X, was supplied from the cleaning solution holding tank 14 through the first pumping means 30 to the two-phase generating module 12 for 10 minutes. The entire process was controlled with the aid of the controller 600.

The process parameters used in this example were: a) gas pressure; 20-30 psig; b) liquid to gas ratio between 1/600 to 1/800; c) gas inlet velocities in the range of 100 to 200 ft/sec; d) temperature of the two-phase mixture, 45° C.

The tubes were then rinsed using two-phase flow for 5 minutes, as described in Example 1. The tubing were then extracted three times with 50 ml Peptone-tween to recover any remaining organisms as per accepted good laboratory practice (GLP) industry protocols. The eluted samples were then cultured to enumerate CFU per tubing. The results of this test showed that the above cleaning achieved complete removal of the Bacillus spores, a 6.2 log reduction (99.999%). The results are shown in Table 2 II.

TABLE II

| Channel | Counts after Exposure (CFU) | Percent Reduction | Log Reduction |
| --- | --- | --- | --- |
| Large dia. tube | <1 | <99.999% | 6.2 |
| Small dia. tube | <1 | <99.999% | 6.2 |

Example 5

This example describes cleaning an endoscope having a complex network of channels as in FIG. 4. All the internal channels of two Pentax gastroscopes Model EG-2901 were inoculated with $2 \times 10^6$ Bacillus subtilis spores dispersed in British soil. The concentration of spores in British soil was $10^9$/ml.

Cleaning was done using the apparatus 100 by connecting the inlets of endoscope internal channels to the inlet adapter 56 and by confining the outlet to the outlet adapter 58. Cleaning and rinsing were done as described in Example 1. The endoscope was cleaned and rinsed according to the following process steps (protocol):

a) Two phase cleaning: Pressure: 20-30 psig; liquid to gas ratio, 1/600-1/800; velocities, 100-200 ft/sec; temperature, 45° C.; cleaning time, 10 min.

b) Rinsing with pulsation: Pressure, 20-30 psig; temperature, 25° C.; rinsing time, continuous water flow for 5 minutes followed by intermittent air flow for 3 seconds after every 6 seconds;

c) Drying: Pressure, 20-30 psig; temperature, 45° C.; drying time, 2 min.

The individual channels of the two endoscopes used in this example were then extracted three times with 50 ml Peptone-tween and cultured according to industry standards. The results of this test are shown in Table III. It is clear that the process and the apparatus of this invention are capable of achieving high log reduction by the two phase flow cleaning method.

TABLE III

| Channel | Corrected counts after exposure to two-phase flow process (CFU/channel) | Percent Reduction | Log Reduction |
|---|---|---|---|
| Endoscope #1 Air/water channel | 1.0 | >99.999% | 6.2 |
| Endoscope #1 Suction/biopsy channel | 15.1 | >99.99% | 5.0 |
| Endoscope #2 Air/water channel | 3.0 | >99.99% | 5.7 |
| Endoscope #2 Suction/biopsy channel | <1 | >99.999% | 6.2 |

Example 6

This example describes cleaning of tubing contaminated with mature biofilm and illustrates the importance of adjusting the liquid to gas.

A 1.4 mm internal diameter tubing having a length of 24 inches (L/D=435) was covered with a highly adherent biofilm on its interior surface and cut in three equal sections, designated as A, B and C.

Section A was used as a Control. It was cleaned by scraping the biofilm with a scalpel and found to contain a total of $2.5 \times 10^8$ CFU.

Section B was cleaned in a slug flow regime by mixing air and a cleaning solution containing 0.15% Tergitol-1X, 1% of SPT and 0.18% of sodium silicate at a liquid to air ratio of 1:1 to 1:10 for ten minutes. The inlet air pressure was 60 psig.

A total of $2.5 \times 10^8$ CFU was found, indicating that the cleaning using the slug flow regime at the above liquid to air ratio was not effective to remove biofilm.

Section C was cleaned with the same cleaning solution with two phase flow according to the method and apparatus of this invention. A two phase flow mixture with a liquid to gas ratio of 1:920 was applied for 10 minutes at 60 psig air pressure.

A total of 800 CFU was found, indicating that the present method is effective to remove highly adherent biofilm.

A comparison of the cleaning results performed at a high gas to liquid ratio with those performed at a low gas to liquid ratio (slug flow) demonstrates that the apparatus and method of this invention achieve effective removal of highly adherent biofilm or residues.

Example 7

This example describes the apparatus and process for cleaning tubular membrane filters either individually or in series according to this invention. The cleaning solution contained an amphoteric surfactant and potassium hydroxide and had a pH of 12.8.

A rather large tubular filter having a length of about 6 feet including 8 individual tubes connected in series, an overall flow length of 48 feet, having a flow path with a total of seven return bends of 180 degrees each, available from the Zenon Environmental Co. of Ontario, Canada, was used as an ultrafilter during a wastewater treatment operation. The tubular membrane was Zenon MT-100 having a molecular weight cut-off of about 100,000. The inside diameter of the tube was about 0.8 inch.

Waste water was supplied to the inside of this tube and clean water was extracted from the outside. During cleaning, the air supply pressure ranged from 40-80 psig. The flow rate of air was 120 standard cubic feet per minute. The velocity of the air was calculated to range from about 40 m/s near the inlet to about 175 m/s near the outlet. The Reynolds number of flow of air in these tubes was 225,000.

The filter was treated by a controlled synthetic wastewater until its flux decreased to 39% of its as-manufactured value. The filter was then cleaned by the two-phase cleaning method using several steps, including both acidic and alkaline cleaning liquids. Using an air to liquid ratio of 200:1, and an alkaline surfactant for 3 minutes, the flux recovered to 64% of its initial value. Applying the two-phase flow for another 2 minutes improved the flux to 81% of its initial value. A slight further improvement in the flux values was realized when the direction of the two-phase flow was reversed.

These results show that a total of five minutes cleaning of a tubular filter using two-phase flow is sufficient to restore the flux values and compares favorably with conventional cleaning requiring a much longer period of time.

This experiment also illustrates the re-formation of the mixed-phase flow condition after a sharp change of direction. At each return bend it can be expected that there might be some disturbance of the mixed-phase flow condition, such as coalescence of droplets, but the successful cleaning results show that there is rapid re-formation of the mixed-phase flow condition after a flow irregularity, such as a bend.

Example 8

Using the same type of filter and cleaning solution as in Example 7, the filter was fouled by a controlled wastewater to the point where its flux level dropped to 35% of its initial value. Cleaning was performed and then stopped, while the flux was measured briefly using the controlled wastewater. Cleaning was resumed, and this was repeated several times until it became apparent that no further improvement was obtained. After three intervals of such cleaning, all at the same mixed-phase flow conditions, the flux level reached a plateau of about 74% of the baseline and no further improvement was obtained. To obtain further improvement, soaking was initiated because both the surface and pore structure of the tubular membrane had become fouled. For a period of time, the passageway was filled with foam which was stationary, and pressure continued to be applied in the same direction as normal operation of the filter. This allows the cleaning solution to reach deeper into the pores. This hold and soak cycle lasted 2 minutes, and was followed by the application of two-phase flow for 15 seconds to remove any newly-dislodged residue. The soaking brought a further improvement up to 95% of the baseline value.

Example 9

Three additional filters were cleaned using the cleaning solution of Example 7. Two of them had been fouled by normal use until the flux was about 40% of its initial value, and one had been fouled by normal use until the flux was only 4% of its initial value. The cleaning cycle included several minutes each of two-phase flow and a holding period, with internal pressure under static conditions. A light backflushing was then performed using the liquid cleaning solution pressurized on the permeate side to several psi.

For the most heavily fouled filter, a further treatment was performed using an acidic two-phase flow cleaning for three minutes, followed by an alkaline two-phase flow cleaning for three minutes. The first two filters were restored essentially to 100% of their initial flux, and the last was restored to about 95% of its initial specified flux.

Example 10

This example describes the cleaning of C-I-P piping systems including tubing, fittings, valves, pumps and other equipment used in C-I-P systems of dairy, food, beverage, cosmetics, pharmaceutical and similar process industries. The piping system used in this example included over 200 feet of sanitizing stainless steel pipe with an internal diameter of 2.0 inch. This pipeline system was arranged with several bends and turns to simulate a typical dairy, beverage or pharmaceutical pipeline system used in industry. The pipeline system had numerous test sections placed at different locations within the piping system that could be removed for inspection to determine the cleaning, rinsing and sanitizing efficiency and then replaced back into the piping system for regular operation. To generate a two-phase flow for cleaning this pipeline system, a special compressor with 450 SCFM capacity was used as the air source. This air source was capable of supplying air flow at pressures over 30 psig and could be regulated at any pressure through a pressure regulator. The two-phase flow used to perform cleaning, rinsing and sanitizing this pipeline system was generated by using a special two phase generating module including the arrangement of air and liquid delivery design as shown in FIG. 2A and using the apparatus of FIG. 1.

The nozzle used to generate droplets for the two phase flow used in cleaning, rinsing, and sanitizing the pipeline was designed to supply liquid droplets in the range between 25 to 400 microns using three different pumps. The process steps for performing the entire cleaning, rinsing and sanitizing cycles were controlled. First, initial testing to determine gas and two-phase flow velocities at the inlet and outlet of the piping system was performed. Water was supplied at different flow rates to the two-phase generating module 12 through the third pumping means 34. Air was regulated using a pressure regulator 42 and a flow meter 50 to cover an air pressure range between 10 to over 30 psig. The two phase flow delivered to the piping system through the inlet adapter 56 was controlled to provide two phase flow having pressures between 12-32 psig and liquid flow rates ranging from 0 to 1.2 gpm. The air and liquid flow rates used in this experiment covered gas to liquid ratios between 900:1 to 27,000:1.

The type of flow going through the pipeline system was observed through transparent sections within the pipeline system. It was found that two phase flow mixtures applicable for cleaning, rinsing and sanitizing the pipeline system can have liquid to gas ratios between 1:1000 to 1:6000. The gas flow rate was determined in these experiments using the flow meter 50.

These sets of experiments showed that the inlet velocities to the passageway system 400 is in the range between 63-110 ft/sec depending on the pressure and the gas to liquid ratio used. Outlet two-phase velocities of the piping system was between 114 to 350 ft/sec.

These experiments provided the conditions to generate two-phase flow with a known gas to liquid ratio, velocity, appropriate setting of first, second, and third pumping means and pressure regulators. These parameters were input into the PLC program of controller 600. During these experiments, the two phase flow mixture exiting the pipeline system was discharged through the mist separator 500 via the outlet adapter 58 and line segments 144, 146, 148 and 152.

Standardized residues and soiling methods were selected for the pipe surfaces to be cleaned and for the removable test panels. Raw milk was applied and dried according to specific industry protocols. These soiling protocols were previously determined to constitute a severe challenge for cleaning with fully flooded conventional C-I-P cycles using conventional chemistries and current cleaning protocols in the dairy industry.

The method of inspection and surface analysis to objectively determine the nature and extent of residue removal were selected based on extensive prior experience and validation. Initial needs to rank relative cleaning performance were satisfied by visual and qualitative evaluation. Relative ranking from 0-10 was used, 10 being clean, 0 being heavily soiled. Baseline cleaning performance data was generated by preparing the milk residues and soiling of pipe and test panels and then executing conventional C-I-P cycles chosen to be representative of industry practice. A set of test panels from these runs were used as controls to determine the cleaning efficiency.

As a control, a conventional fully flooded CIP cycle was used to establish a baseline to be used to compare the efficiency of cleaning, rinsing and sanitizing pipeline systems as follows:

Step1—Preflushing the line with water: Time, 3 min; vol. of water used, 90 gallons; temperature, ambient.
Step2—Drain 1: Time, 0.5 min.
Step3—Cleaning step: Time, 12 min; vol. of water used, 90 gallons; vol. of cleaning sol. Used, 60 gallons; chemistry, alkaline with hypochlorite bleach; temperature, 150° F.
Step4—Drain 2: Time, 0.5 min.
Step5—Rinse: Time, 3 min; vol. of water used, 90 gallons; temperature, ambient
Step6—Drain 3: Time, 0.5 min.
Step7—Sanitizing: Time, 2 min; vol. of water used, 90 gallons; sanitizing solution vol., 60 gallons; chemistry, peracetic acid based; temperature, ambient.
Step8—Drain: Time, 0.5 min.

Thus this fully flooded C-I-P cycle takes 22 minutes, consumes 360 gallons of water and 120 gallons of cleaning chemicals and sanitizers. The test panels placed at different locations (30 feet apart) were inspected and were rated between 3 and 5 on the cleaning efficiency scale, i.e., the panels still showed some remaining residues and had hazy spots.

Several tests to perform the two-phase flow cleaning of the pipeline system using apparatus 100 were performed to determine the range of effective operating conditions to clean milk residues. The following experiments were performed:

Test Series 1

Multiple tests were performed to determine the cleaning efficiency of the pipeline system contaminated with dried milk residues as described above. In this series of tests, the effect of air pressure and gas to liquid ratio on cleaning efficiency was evaluated. Air pressure to form the two-phase flow was in the range between 8-32 psig; gas to liquid ratio was adjusted between 1400:1 to 15,000:1. To achieve these conditions, the air flow rate was measured by the flow meter 50 at different pressures. The liquid flow rates were varied between 0.12 to 2.0 gpm by adjusting the first pumping means 30 with the aid of controller 600. Again, test sections were installed and removed to determine cleaning efficiency using the 0-10 scale as described above.

In further experiments, the inlet air pressure was kept constant at 12 psig using the air source 10 and the regulator 42 of apparatus 100. The cleaning liquid level was varied between 0.12 to 1.2 gpm, giving rise to gas to liquid ratios between 12,000:1 to 900:1, respectively. The cleaning time in all cases was kept constant at 5 minutes. Cleaning efficiency results were measured by inspecting the test sections as described above. The results of these experiments showed that a gas to liquid ratio between 2,000:1 to 6,000:1 achieve effective cleaning (cleaning scale=6-7) at an air pressure a) of about 12 psig.

The results of this series of tests showed that air pressures between 8 to 32 psig, gas to liquid ratios between 1400:1 to about 6,000:1 and cleaning times between 5 to 10 minutes produced high cleaning efficiency rated between 7-9 on the 0-10 scale as described above. Based on these experiments, air pressure of about 10 psig or more, and gas to liquid ratios between 1,400:1 to 6,000:1 appear to provide effective cleaning of the pipeline system. The use of alkaline cleaning solution including a hypochlorite salt, as conventionally practiced in dairy C-I-P cleaning, appears to provide additional advantages when used in the two-phase cleaning at the conditions described above. The two phase mixture inlet velocity range optimal for cleaning this system was between 60 to 100 ft/sec, preferably above 70 ft/sec.

Test Series 2

A comprehensive testing was performed to determine the practical ranges for using the two-phase flow method and apparatus 100 to perform cleaning, rinsing and sanitizing of pipeline systems used in dairy, food, beverage and pharmaceutical processing. The following process steps were identified as a guideline:

Step1—Air purge: Time, 0.5 min.

Step2—Two phase pre-flushing/pre-cleaning: Time, 4 min; liquid flow rate 1.2 gpm; gas pressure=12-15 psig; gas to liquid ratio about 1,000:1; chemical, alkaline cleaner with hypochlorite bleach; temperature, ambient.

Step3—Two-phase flow cleaning cycle: Time, 5 min; liquid flow rate, 0.22 gpm; gas pressure, 12-15 psig; gas to liquid ratio about 1400:1-7,000:1; chemical, alkaline cleaning solution with bleach; temperature, ambient.

Step4—Two-phase rinsing: Time, 3 min; pressure, 12-15 psig; gas to liquid ratio about 1,000:1; liquid flow rate, 1.2 gpm; temperature, ambient.

Step5—Air purge: Time, 0.5 min.

Step6—Two phase sanitizing: Time, 3 min; pressure, 12-15 psig; gas to liquid ratio about 1,000:1; liquid flow rate, 1.2 gpm: sanitizing chemical, peracetic acid based sanitizer; temperature=ambient.

Test results of several runs according to the above process achieved equivalent or better cleaning results compared to conventional fully flooded C-I-P systems. The cleaning efficiency scale of two phase cleaning ranged between 7-9 as compared to 3-5 for fully flooded C-I-P cleaning however.

The results of this example demonstrate that two phase flow cleaning is effective and practical for applications in dairy pipeline cleaning and similar pipeline systems. The use of apparatus 100 and the process outlined above achieved 25-40% savings of time, over 95% savings of water, over 90% savings of cleaning chemical solution and considerable savings in sanitizing solutions.

Example 11

In this example, we describe methods and apparatus for removing old biofilm from a fluid distribution system consisting of pipes, tubing, valves and connections. Examples of such distribution systems include, but are not limited to, modern water systems, dental chair water circuits, dialysis machines, such as those used in hemodialysis, respirator and ventilation tubes, such as those used in hospitals where biofilm is known to quickly grow and cause infection, water coolers, beverage dispensing systems and multiple other applications in the food, beverage and pharmaceutical industries and the like. This example specifically pertains to the water circuit in dental chairs and includes a study that elapsed over a nine-month period. Eight dental chairs were equipped with apparatus 100 and the dental chair waterlines were connected as the passageway to be cleaned 400 in apparatus 100 as shown in FIG. 1. The dental units used in the study were 11 years old and were supplied with municipal water during this period, without changing their tubing. The dental unit waterline circuits were covered with old and mature biofilm, with the presence of extensive layers of inorganic scale at the surface of the tubing due to the hardness of the water supply. These dental units had to be cleaned to remove the old biofilm, as well as the heavy inorganic scale, in order to bring them into compliance with the 200 CFU/ml level, as recommended by the American Dental Association (ADA) for dental water quality.

First, the units were connected to adapters 56 and 58, using the arrangement and treatment described in Example 3. To perform the initial treatment, the unit was treated with a two-phase flow mixture with a high pH composition containing sodium hypochlorite bleach according to the following composition: 5 wt. % sodium meta-silicate, 0.5% Tergitol-1X. The treatment was done for 10 minutes and covered all the lines in the dental chair. The bioburden in dental treatment water was reduced from $10^7$ to about $10^3$ CFU/ml.

The dental units were then cleaned daily with the two-phase flow process using apparatus 100 as described in Example 3, and the CFU/ml was monitored daily. After two weeks of monitoring, bacterial counts in some dental units remained high, around $10^3$ CFU/ml. Upon SEM examination of the surface of the dental tubing, it was discovered that a heavy layer of inorganic scale was present on the surface and needed to be removed to achieve complete removal of old biofilm from the entire surface of the water circuit of non-complying dental units.

To remove scale, the two-phase flow process was used as described in Examples 3, except using a de-scaling solution having the following composition: 3% hydroxyacetic acid and amphoteric surfactant, pH 1-2. After treating the water circuit of dental chairs with multiple two-phase cleaning cycles using the de-scaling agent defined above as the liquid phase, complete removal of the inorganic scale was achieved as per SEM examination. Then the units were brought into compliance with the 200 CFU/ml level recommended by ADA. This low bacterial level was maintained by performing a daily cleaning with the two-phase flow process as described in Example 3.

We discovered that the use of the two-phase flow process combined with the alkaline compositions having a high pH in the presence and absence of hypochlorite bleach to be effective in removing old or highly adherent biofilm.

To arrive at this composition, a series of liquid compositions were made covering pH ranges from 2 to 13.5 and applied using the two phase flow cleaning process to dental tubing extracted from the 11-year old dental units mentioned above. We discovered that compositions based on the above formula having a pH of less than 10.0, and applied with the two-phase flow process do not achieve removal of biofilm matrix using SEM and optical microscopy examination. Compositions having an acid pH were found to be very ineffective in removing biofilm from tubing surfaces. However, as the pH of the cleaning solution was increased to above 10, some matrix removal was observed; but some highly adhering biofilm spots remained on the surface of the tubing even when the cleaning was performed with high two-phase flow velocity of about 100 ft/sec. Increasing the pH of the above composition by increasing the level of sodium meta-silicate or NaOH to above 12.5 was needed to achieve complete removal of the very old biofilm with the two-phase flow process, carried on only for about 5-10 minutes. This high pH level may be essential in ionizing the hydroxyl groups of sugar moieties of the polysaccharide matrix, thus resulting in lowering adhesion to the surface of tubing during the two-phase flow cleaning. Therefore, a combination of high-pH liquids applied in the form of two phase flow, at velocities above 100 ft/sec, was necessary to remove highly adhering biofilm from tubing or pipes. This result was further confirmed by the results of Example 10 in cleaning dairy pipeline systems and of Example 1 in cleaning dialysis center piping systems.

In this example, the removal of old biofilm and inorganic scale requires the application of two-phase flow cleaning, preferably alternating acid compositions and alkaline compositions with high pH (preferably >12.5) to remove adhering biofilm. This procedure can be repeated several times (2 to 10 times) until all biofilm and scale are removed. The number of times this treatment is required depends on the condition of the surface and the adhesion of biofilm and inorganic scale. The use of highly alkaline liquid compositions with hypochlorite bleach was beneficial in this case to remove mature biofilm. The addition of some two-phase flow cleaning cycles where the cleaning solution included acid de-scaling agents was important in the cases where scale is present. This was also the case in cleaning dairy pipelines where calcium scale deposits are known to form during milk flow. This example demonstrates the process and compositions needed to treat and control highly adhering biofilm in fluid distribution systems.

Example 12

This example describes the apparatus and processes for cleaning and sanitizing the surfaces of tubing, pipelines, membranes and equipments. The example relates to the use of apparatus 100 and the two-phase process to clean, disinfect, sanitize and sterilize the surfaces of passageways of the above-listed applications, and similar passageways that are complex or have high L/D ratio. Two parts of this example illustrate two important cases including applying a sanitizer as a part of the entire two-phase cleaning, rinsing and disinfecting process.

Part A

This example pertains to cleaning and sanitizing the internal channels of endoscopes, which constitute a network of internal tubing having bifurcation and connections, as described in Example 5. A surrogate endoscope was manufactured from clear plastic tubing including a suction channel, an air channel and a water channel, similar to the arrangement used in gastrointestinal endoscopes made by the Pentax Company. The clear tubing was used to define the two-phase flow that is optimal in cleaning and sanitizing internal channels of this network of tubing. Visual observations were made either with the naked eye or with the aid of an optical microscope. Gas:liquid ratio, liquid composition and two-phase flow velocities were varied using apparatus 100 with the aid of a controller 600. Observations were made and results collected for several experiments.

In cleaning experiments, the transparent surrogate endoscope was contaminated with Hucker's soil (peanut butter, 10 g; butter, 10 g; flour, 10 g; lard, 10 g; dehydrated egg yolk, 10 g (or two fresh eggs); evaporated milk, 15 ml; distilled water, 50 ml; Higgins India ink, 4 ml; International printers ink solution (A646 diluted one to one with 10 drops boiled Linseed oil), 20 drops); Normal saline, 3 ml; dehydrated blood, 1 g) and allowed to dry for periods ranging from two hours to overnight. The endoscope was then connected to inlet adapter 56 and outlet adapter 58 of apparatus 100, as described in Example 5.

Two-phase cleaning was done using the following conditions:liquid to gas ratio—1/600 to 1/800; gas velocities: 100 to 200 ft/sec; gas pressure 20-30 psig; cleaning time, 10 min.

Judging by the removal efficiency of black-stained Hucker's soil, we found that the creation of liquid droplets in the two-phase cleaning was important to the quick and efficient cleaning of the internal channels of the endoscope. Three parameters were found to be important for a successful two-phase cleaning process: a) the gas:liquid ratio, b) the two-phase velocity and c) the nature of the two-phase flow distribution inside the lumen of the channels. If the condition of high velocity is satisfied (above 70-150 ft/sec), full coverage of the entire channel surface by dynamic impact of droplets was found to depend on the gas:liquid ratio, liquid composition, surface tension and wetting properties of the channel surface, including the residue that is deposited over it. Optimal cleaning results were obtained when the two-phase flow produced high-velocity droplets covering the entire surface of the channel along its full length.

When the surface of the channel had areas that were not covered with a liquid film, while other areas were experiencing droplet impact, the cleaning proceeded fast and with high efficiency. In this case, it was apparent that parts of the surface were impacted by droplets and other parts were not wetted by the liquid in a somewhat uniform distribution. It was evident from these experiments that de-wetting processes were taking place during the two-phase cleaning process (especially in the presence of a surfactant); and it appears that this de-wetting process plays an important role in the two phase cleaning. This optimal distribution of droplets over the surface of channels and the presence of areas not covered by liquid were a function of the gas:liquid ratio, two-phase flow velocity and liquid composition (including type of added surfactant and/or solvent), and, to some extent, on the mode and rate of introducing the liquid when forming the two-phase flow at the inlet of the channels.

If the gas:liquid ratio was too high, the flow in the channels resembled that of "rivulet" flow (liquid moved in the form of a streak without providing full coverage of channel surface), and poor cleaning was observed for this flow condition. On the other hand, when the gas/liquid ratio was too low, surface flooding took place and the surface of the channel was covered with a liquid film. The optimal gas:liquid ratio that provided good cleaning was between 600/1 and 800/1 at a velocity range of 100-200 ft/sec, for the case of endoscope channels. Further, we have discovered that different gas:liquid ratios, within this range, need to be somewhat tailored to the cleaning of the narrow air:water channel or to the wider suction channel.

Furthermore, in this example we found that the liquid composition plays a critical part in the behavior of the two-phase flow at the surface of the tube or channel during cleaning, even if such liquid is delivered to give the same gas/liquid ratio. A composition containing sodium tripolyphosphate, 2%; sodium carbonate, 0.6%; Tergitol-1X, 0.15% and sodium meta-silicate, 0.13%, was found to give reasonable two-phase behavior at the surface of the channels when applied at the flow conditions provided above. However, a higher surfactant concentration (to about 0.3 to 0.5%) led to excessive surface wetting of the channel surface and hampered the removal of Hucker's soil. In addition, it was found that the type of surfactant alters the behavior of the two-phase flow at the surface of the channel during cleaning.

For example, when surfactants Tego Betaine ZF, made by Goldschmidt Chemical Corporation, Surfactants XTJ 504 (or 597), made by the Huntsman Company, or sodium dodecyl sulfate were used, instead of Tergitol (1X or 2X) surfactant, excessive surface wetting and foaming were encountered, and this resulted in a significant decrease in the effectiveness of the cleaning. It is thus important to select the type of surfactant, its level and its wetting and de-wetting dynamic properties at the surface of the tube or channel. In addition, we also found that the addition of alcohols, such as isopropanol or the like, in the cleaning solution, causes excessive surface wetting, and again hampers the cleaning of the Hucker's soil when using the two-phase flow process. These factors demonstrate the importance of the above parameters in achieving effective cleaning.

Part B

This example addresses the use of sanitizers to achieve disinfection with the two-phase flow process after the conclusion of the cleaning step as described in the examples. In some applications, when the amount of liquid sanitizers such as bleach, peroxyacids, iodine and the like is very large, the use of the two-phase flow method to sanitize the surface after cleaning is preferred, in order to reduce the amount of sanitizers used. This is clearly demonstrated in Example 10, where effective sanitization could be accomplished at a high gas:liquid ratio, which translates to a very small fraction of sanitizer volume compared to fully flooded C-I-P systems.

We found it is best to apply the sanitization step at the conclusion of the cleaning step according to the two-phase flow process. When the cleaning is performed with the two-phase flow process, the surface to be sanitized will be practically free of microorganisms, and the demand for employing high sanitizer concentrations, or using long exposure times, will be reduced.

In one case, the pipeline system used was the same as discussed in Example 1. The sanitizing step was performed with an alkaline hypochlorite bleach solution applied in the two-phase flow mode, at a gas/liquid ratio between 600/1 and 800/1 for 5 to 10 minutes. Culture results of the surface showed no viable count, i.e., zero $CFU/cm^2$. In this example, only about 1-2% sanitizing solution was used to perform the two-phase sanitizing step with results similar to those obtained in fully flooded liquid C-I-P system.

This same experiment was repeated but using peracetic acid solution (0.1-0.2%) as the liquid fraction of the two-phase mixture; similar results were also achieved (0 CFU/$cm^2$). In the above cases, the sanitizing step was run using apparatus 100 and the gas:liquid ratio was adjusted within the range defined in Example 1.

Example 13

Cleaning apparatus 100 and the two-phase cleaning process were used to perform clean-in-place (C-I-P) operations of reverse osmosis (RO) membrane elements, part of a wastewater system, with noted success. In this case, the system to be cleaned 400 consisted of a single 4 inch RO pressure vessel (made by Osmonics Corporation) having two spiral wound RO elements (FilmTec TW30-2540) connected in series. The above RO pressure vessel was piped with a feed inlet, a permeate outlet for purified water and a concentrate outlet.

This single-vessel RO membrane system was integrated into a pilot plant used to treat a high total suspended solids (TSS), high total dissolved solids (TDS), salt, protein (whey) and fat laden dairy wastewater from a dairy plant washdown. This wastewater was first pretreated using a submerged Kubota FC-25 microfilter (MF), operated as a bioreactor, to reduce the total suspended solids from >10,000 ppm to <100 ppm, and to lower the biological oxygen demand (BOD) of this waste stream. The MF effluent was fed into the RO vessel described above to produce RO water. The latter RO step was a single separation stage with 28% recovery and with means for recirculating the concentrate to a RO feed holding tank. Due to this configuration, there was a rapid increase in the RO feed quality, which had a TDS of over 8,000 ppm on the average. The resulting fouling and scaling in the RO membrane caused significant reduction of RO flux in a matter of hours to less than 50% of design specifications of the RO membranes. RO flux, TDS, pH and temperature data were documented during a three-month study for this system. In addition, water quality of the micro-filtration feed, RO pretreated influent and RO products was measured daily over a period of five weeks.

Apparatus 100 was used to clean the above RO membranes (two RO elements connected in series in a single pressure vessel) on a periodic basis. To connect the RO pressure vessel to apparatus 100 and to allow the application of two-phase CIP cleaning during normal production of purified water, a special cleaning adapter, as shown in FIG. 5, was developed to separate the permeate stream from the rest of the system during the cleaning step.

The adaptor 415, as shown in FIG. 5, connects the pressure vessel with the aid of two clamps, 430 and 434. The permeate channel of the RO spiral element in the pressure vessel becomes tightly sealed to this adapter through sleeve connector 424, which separates the permeate channel from the two-phase mixture during the cleaning cycle. The permeate liquid port 420 is sealed with a welding joint 436 in a way so as to prevent contact with the cleaning solution. The RO spiral membrane is designated as 428 and the body of the adapter is shown as 432.

During cleaning, the permeate channel is closed with a valve (not shown) connected to the permeate port 420, which is open during the filtration operation and is closed during the cleaning step. The two-phase mixture 422 is created in the two-phase generating module 12 (FIG. 1) where the liquid fraction is delivered by the first pumping means 30 to a special nozzle 13, see FIG. 2A, that delivers liquid droplets in the range of 25 to 400 microns in size to the liquid inlet port 214 of the two-phase generating module 12. The two-phase flow is generated in the module 12 by propelling the droplets with a gas stream from the gas or air source 10, as described in Example 1. This two-phase mixture is directed to the inlet adapter 56, which is connected to the adapter shown in FIG. 5, to convey such two-phase mixture to the feeding channels of the RO membrane. The direction of flow is clearly shown in FIG. 5 where the two-phase flow is directed to inlet 418 through the adapter 415 and then to the feeding channels of two spiral wound membrane elements 428 connected in series. The two-phase exhaust emerging from the end of the feeding channels of the second membrane element is connected to the outlet adapter 58, and then discharged though the mist separator 500 as described in Example 1.

A typical two-phase cleaning cycle of membranes of this type requires using air pressure in the range of 30 to 50 psig. In the case of the fouling described above, the air pressure was 50 psig. The two-phase flow process used in cleaning involved the use of a two-step cycle. The first step involved two-phase cleaning with an acid cleaning agent supplied from cleaning solution holding tank 16, and the second step was performed with an alkaline cleaning solution supplied from cleaning solution holding tank 14. Both were delivered through first pumping means 30 to the two-phase generating module 12, see FIG. 1. In each case, the mixture was delivered to the RO elements via the feed adapter 415. The cleaning steps with acid and base were carried out for 10 minutes each. After completing the above two-phase cleaning steps, the RO elements were rinsed for 10 minutes with the two-phase process by supplying water from the rinse water holding tank 20 with the aid of the third pumping means 34. The entire process as described above was pre-programmed and controlled by the controller 600.

The data obtained from operating this C-I-P system over a period of three months indicated that membranes fouled with dairy, milk and whey residues that were reduced to below 50% of their normal/clean flux, could be restored and maintained to 80-90% of design specification using a 10-minute cleaning cycle consuming only 4 liters of dilute cleaning solution. The results are shown in Table IV, which shows examples of RO flux data before and after cleaning for four cases. In order to obtain accurate RO flux performance results, the temperature of the RO feed water and the net driving pressure across the RO membrane (indicated by TDS) were taken into account.

Cleaning for cases 1 to 3 was performed with the two-phase flow using an alkaline cleaning solution only; this cleaning process was sufficient to bring the RO flux back to above 86% of manufacturer's specifications. However, as inorganic scale builds up on the membrane surface, thus two-phase alkaline cleaning alone was not sufficient to remove all foulants.

In Case 4, two-phase alkaline cleaning only brought the RO flux performance back to 63% of new performance. However, an additional two-phase acidic cleaning step, following the alkaline cleaning step, brought the RO back to 88% of the new performance flux level. The results are shown in Table IV below, wherein the RO flux is given in liters per minute, as the manufacturer specification (Mfr specs)

In Table IV the RO flux is given as liters per minute, as the manufacturer specification (Mfr specs).

TABLE IV

| Cleaning Case | RO Flux (lpm) Before | RO Flux (lpm) After | Cleaning Solution | Mfr specs (lpm) | Performance Recovery |
|---|---|---|---|---|---|
| 1 | 2.54 | 3.19 | Alkaline | 3.47 | 92% |
| 2 | 2.95 | 2.97 | Alkaline | 3.47 | 86% |
| 3 | 3.38 | 3.50 | Alkaline | 3.47 | 100% |
| 4 | 1.39 | 2.18 | Alkaline | 3.47 | 63% |
|   |      | 3.07 | Acid     | 3.47 | 88% |

Other configurations of spiral membrane types in pressure vessels, a different number of elements per pressure vessel, or a different arrangement of the membranes would all obtain similar results after treatment.

Example 14

This example relates to cleaning spiral wound membranes of any type including those used in microfiltration, ultrafiltration, nanofiltration and reverse osmosis separation processes used in water treatment, desalination and purification, and in industrial processing such as dairy, food, beverages, pharmaceutical, chemical, oil and gas and other industries. The spiral wound modules in this example were used in municipal water production, and were fouled with inorganic scale, biofilm, humic substance (natural organic matter—NOM) and silt as per our microscopic examination of dissected membrane surfaces. The flux of such membranes had declined to below acceptable levels and the pressure drop (between the two ends of the membrane) increased to a level such that the membranes were rendered unusable.

Attempts to clean these membranes using a conventional liquid circulation process with an alkaline cleaning agent for 8 hours followed by additional four hours with acidic cleaning agent was not successful, i.e., the flux and pressure drop between the two ends remained below acceptable levels. These membranes were 8 inch RO spirals used for about six months in municipal water production and were made by Hydranautics, Model number CPA-2. These RO spiral modules were cleaned with the two-phase process using apparatus 100 with noted success.

To perform cleaning, the spiral module was first connected to adapter 415 of FIG. 5 in order to separate the permeate side from the feeding side of the membrane during the two-phase cleaning, as described in detail in Example 13. The spiral element was then connected to the inlet adapter 56 and the outlet adapter 58 of the passageway to be cleaned 400 of the apparatus 100 as shown in FIG. 1. For the purpose of cleaning membranes according to this invention, the spiral elements were connected to apparatus 100 such that the highly fouled end of the module was connected to the outlet 58 to facilitate contaminant removal from the end where they were deposited. This arrangement is preferred in order to directly push the contaminants out of the membrane module to the discharge end, and at the same time to prevent contaminating the less fouled portion of the membrane module. The highly fouled end of a spiral module is normally the end where the liquid feed enters the module during the separation process.

The gas source used in this example included a 50-HP compressor, two air filters and six-240 gallons air tanks to store the air needed for cleaning purposes. The air was regulated with a pressure regulator 42 and a pressure gauge 44, and its flow rate was measured by a flow meter 50. The cleaning process in this example included application of a two-phase cleaning step using acid and alkaline cleaning agents as the liquid fraction of the two-phase mixture. Other steps for soaking the surface of the membrane for a period of time to condition and weaken the adhesion of foulants is used before the application of the two-phase cleaning step. The cleaning protocol employed in this example included rinsing with water after the conclusion of the two-phase cleaning steps to restore the function of the membrane as required for separation processing.

To perform the cleaning of the spiral elements described above, air pressure was set at 45 psig using the pressure regulator 42 and the air flow was conveyed to the two-phase generating module 12 as described in the previous examples. Cleaning liquids (alkaline or acidic) were supplied from cleaning solution holding tanks 14 and 16 with first pumping means to the liquid inlet 214. The two-phase generating module in this case was the same as described in Example 13 and shown in FIG. 2A, with the use of a nozzle that deliver the liquid at droplet size 25-400 microns. The use of droplet size distribution in this range or even smaller (30-200 microns) was found to be important in establishing the two-phase flow for cleaning spiral wound membranes. The liquid was fed at rate between 0.1 to 0.2 gallons/minute, using the first pumping means with the aid of a controller 600 of apparatus 100. The two-phase mixture formed by the above means was propelled to enter the feeding channels of the spiral wound membrane. The two-phase flow with droplets was arranged such that the entire surface at the entrance of the feeding channels was covered with droplets, and no flooding conditions were allowed at the entrance section of the spiral wound membrane. Cleaning was done in both vertical (from top down) or horizontal directions, as long as the two-phase velocity was high enough as given in this example. During cleaning, the two-phase mixture that emerged from the end of the modules was conveyed to the mist separator 500 for proper discharge as described in the previous examples.

Cleaning of spiral membranes in this example was performed at an inlet air set pressure between 20 to 55 psig and at cleaning liquid delivery flow rates between 0.052 and 0.3 gallons/minute. The gas/liquid ratio was in the range of 3000:1 and 30,000:1. Two-phase flow cleaning time was between 5-15 minutes. Entrance air velocity that was found to be effective in two-phase cleaning was about 25-30 feet/second or higher, but over 30 feet in at least in some portion of the modules is preferred. This ratio may shift depending on the nature of foulants and their adhesion to the surface of the membrane.

To achieve these conditions, sufficient air volume is needed to reach these velocity values in the feeding channels of spiral wound membranes. As gas expands inside the membrane feeding channels when the two-phase flow travels though them, higher velocities are generated at the highly fouled end of the membrane, where the two-phase flow exits the membrane. Exit velocities between 40 to 70 feet/second were estimated from our experiments. We discovered that two-phase cleaning average velocities between 24 to 30 feet/second to be significant for cleaning spiral wound membranes. Flux recovery of fouled spiral membranes was not significant until these velocity values were reached, and cleaning at below these values produced very little improvement in membrane flux.

The nature of the two-phase flow inside spiral wound membrane channels is more complex to describe due to the presence of spacers between the channels, but should be similar to the flow in small tubes such as those described in Examples 3 and 4. Formation and re-formation of droplets, and generation of high shear stresses represent the general features of the two-phase flow for this membrane configuration.

During cleaning with two-phase flow, we also discovered that a highly turbid suspension is generated during the first 1-3 minutes of the cleaning process, as judged by collecting the liquid fraction from port 82. This observation indicated that this cleaning process is effective in removing solid-particle foulants such as silt, clay or sand from membrane feeding channels during the cleaning process. This discovery supports our findings that a significant improvement in pressure drop values (between the two ends of the membrane) is accomplished when cleaning is performed with the two-phase process, as compared with liquid circulation methods. The shear forces and mass transfer rates achieved in the feeding channels of the spiral wound membrane during two-phase cleaning appear to be high enough to efficiently remove types of foulants that are responsible for the deterioration of the pressure drop as defined above.

Five cases were investigated to define the two-phase conditions needed to recover flux and pressure drop (as defined above) of fouled 8-inch spiral modules. The 8-inch spiral modules that were fouled during municipal water production were used in the experiment. Cleaning was performed using apparatus 100 with the aid of the adapter 415 (see FIG. 5). The cleaning was performed at the conditions given in Table 4 to obtain entrance velocity of two-phase flow of about 30 feet/second. The results showed that optimal cleaning was achieved at air pressures between 20-50 psig and preferably about 40-50 psig for this case. The gas:liquid that gave nearly optimal results was about 4000:1 at the entrance of the membrane. The two-phase cleaning was performed with an alkaline cleaning agent at pH 11-12 and had about 0.1% of a non-foaming non-ionic surfactant (Tergitol 1X—made by the Dow Chemical Corporation). It was found that prior soaking by circulating the cleaning agent for 30 to 60 minutes at 40-50° C. to be beneficial in reducing the time of two-phase cleaning to about 5-10 minutes. The membranes cleaned as above were then rinsed using two-phase flow with water, and the flux and pressure drop were then measured. In all the cases tested, the pressure drop decreased from about 15 psi to <7 psi after the two-phase cleaning. Flux values before and after the two-phase cleaning are given in Table 6 below.

A summary of the cleaning conditions are given in Table V below.

TABLE V

| Case | Set Pressure* (psi) | Run Pressure** (psi) | SCFM | Air Velocity (ft/3) In | Air Velocity (ft/3) Out | Liquid Rate (gpm) | Air/Liquid In | Air/Liquid Out |
|---|---|---|---|---|---|---|---|---|
| 1 | 20 | 7 | 394 | 32.0 | 47.0 | 0.052 | 37900 | 55690 |
| 2 | 25 | 10 | 448 | 32.0 | 53.4 | 0.052 | 37950 | 63300 |
| 3 | 30 | 12 | 496 | 32.2 | 59.0 | 0.052 | 38900 | 70100 |
| 4 | 40 | 20 | 510 | 26.3 | 60.0 | 0.3 | 5358 | 12450 |
| 5 | 55 | 26 | 627 | 27.3 | 74.6 | 0.3 | 3950 | 14460 |

*Set Pressure is the pressure set at the regulator located at the outlet of gas storage receiver
**Run Pressure is the actual pressure measured at the inlet of the RO housing during cleaning.
The "Out" condition is at 0 psig.

Flux improvement on 8-inch RO membrane using the two-phase cleaning process is shown in Table VI.

TABLE VI

| RO Filter Serial # | Initial Flux (gpm) | Final Flux (gpm) |
|---|---|---|
| 197761 | 0.75 | 3.2 |
| 197686 | 1.2 | 1.3 |
| 197753 | 1.2 | 2.8 |
| 197702 | ~1.0 | 3.0 |
| 196500 | ~1.0 | 2.5 |
| 197763 | ~1.0 | 3.5 |
| 197763 | ~1.0 | 2.8 |

The results in Table 6 demonstrate that the two-phase cleaning apparatus and method is effective to restore the flux and pressure drop in a short cycle of about 5-10 minutes. Pre-soaking appear to soften the foulants and assist in achieving effective two-phase cleaning. Improving flux in this case is significant since application of prior liquid circulation alone over eight hours was unable to improve the performance of the membranes tested.

Cleaning was done in both vertical and horizontal positions with similar results; however cleaning in the vertical position may be preferred. In the horizontal position, we discovered that liquid drainage due to gravity occurs during the two-phase cleaning of spiral membranes and as a result the gas:liquid ratio becomes somewhat lower at the bottom of the module compared to the top cross section. This condition was more pronounced when the two-phase flow velocity was low and gas:liquid ratios were low; however, when velocity was increased to the levels given in this example, more uniform distribution of the two-phase flow in the membrane was obtained. When the optimal flow condition is achieved, the orientation of the membrane (vertical or horizontal) does not appear to affect the cleaning efficiency.

Based on the results of this example, it is predicted that frequent cleaning with the two-phase flow is capable of restoring the flux and maintaining the pressure drop between the two ends of the membrane at acceptable levels. The frequency of cleaning can thus be adjusted based on the fluid stream used in the separation process and the type of residue formed in the internal channels of the membrane.

Although the invention has been described in terms of particular embodiments, the invention is not meant to be limited to the details set forth above. The invention is only to be limited by the scope of the appended claims.

We claim:

1. A method for cleaning an endoscope having internal channels, the method comprising:
   (a) generating a first two phase mixture comprising liquid droplets having a size of about 25 microns to 400 microns in a gas, the liquid droplets comprising an alkaline cleaning solution comprising a surfactant;
   (b) applying the first two phase mixture to the endoscope to provide cleaning of the internal channels of the endoscope, wherein the gas comprises air and the liquid comprises a cleaning solution, at a velocity of about 100 ft/s to about 200 ft/s and a volumetric ratio of gas to liquid of between 600:1 and 800:1; and
   (c) rinsing the cleaning solution from the endoscope by a continuous water flow and intermittent air flow.

2. A method according to claim 1, wherein the step of applying comprises removing bio burden from the internal channels of the endoscope.

3. A method according to claim 1, further comprising:
   exhausting the first two phase mixture from the endoscope into a mist separator for separation of the gas and the liquid.

4. A method according to claim 1, further comprising:
   drying the endoscope.

5. A method according to claim 1, further comprising:
   sanitizing the endoscope with a sanitizing chemical.

6. A method according to claim 4, wherein the step of drying the endoscope comprises continuously circulating the gas through the internal channels of the endoscope.

7. A method according to claim 5, wherein the sanitizing chemical comprises an alkaline based sanitizer.

8. A method according to claim 5, wherein the sanitizing chemical comprises a peracetic acid based sanitizer.

9. A method according to claim 1, wherein the surfactant comprises a nonionic surfactant.

10. A method for cleaning an endoscope having internal channels, the method comprising:
    (a) generating a first two phase mixture comprising liquid droplets having a size of about 25 microns to 400 microns in a gas, the liquid droplets comprising an alkaline cleaning solution comprising a surfactant;
    (b) applying the first two phase mixture to the endoscope to provide cleaning of the internal channels of the endoscope, wherein the gas comprises air and the liquid comprises a cleaning solution, at a velocity of about 100 ft/s to about 200 ft/s and a volumetric ratio of gas to liquid of between 600:1 and 800:1; and
    (c) rinsing the cleaning solution from the endoscope by a continuous water flow and intermittent air flow wherein the intermittent airflow comprises pulsing for about 3 to 6 seconds after every 6 to 10 seconds.

\* \* \* \* \*

UNITED STATES PATENT AND TRADEMARK OFFICE
CERTIFICATE OF CORRECTION

| | | |
|---|---|---|
| PATENT NO. | : 8,083,861 B2 | Page 1 of 1 |
| APPLICATION NO. | : 12/321321 | |
| DATED | : December 27, 2011 | |
| INVENTOR(S) | : Labib et al. | |

It is certified that error appears in the above-identified patent and that said Letters Patent is hereby corrected as shown below:

On the Title page, Item (73) Assignee should read -- Princeton Trade and Technology, Inc., Princeton, NJ --

Signed and Sealed this
Seventeenth Day of July, 2012

David J. Kappos
*Director of the United States Patent and Trademark Office*